US005763568A

United States Patent [19]

Atkinson et al.

[11] Patent Number: 5,763,568
[45] Date of Patent: Jun. 9, 1998

[54] INSECTICIDAL TOXINS DERIVED FROM FUNNEL WEB (ATRAX OR HADRONYCHE) SPIDERS

[75] Inventors: Ronald Keith Atkinson, Toowoomba; Merlin Evelyn Harry Howden, Cattai; Margaret Isabel Tyler, Turramurra; Edward Joseph Vonarx, Jan Juc, all of Australia

[73] Assignee: Zeneca Limited, London, England

[21] Appl. No.: 682,485

[22] Filed: Jul. 17, 1996

Related U.S. Application Data

[63] Continuation of Ser. No. 256,933, filed as PCT/AU93/00039, Jan. 29, 1993, published as WO93/15108, abandoned.

[30] Foreign Application Priority Data

Jan. 31, 1992 [AU] Australia ............................ PL0722

[51] Int. Cl.$^6$ ............................................. C07K 14/435
[52] U.S. Cl. ........................................ 530/300; 530/324
[58] Field of Search ................................. 530/300, 324

[56] References Cited

U.S. PATENT DOCUMENTS 4,855,405  8/1989  Yoshioka et al. ..................... 530/300

FOREIGN PATENT DOCUMENTS

| A-46881/89 | 6/1990 | Australia . |
| 156540 | 10/1985 | European Pat. Off. . |
| 374753 | 6/1990 | European Pat. Off. . |
| 374940 | 6/1990 | European Pat. Off. . |
| 395357 | 10/1990 | European Pat. Off. . |
| 425096 | 5/1991 | European Pat. Off. . |
| 431829 | 6/1991 | European Pat. Off. . |
| 436332 | 7/1991 | European Pat. Off. . |
| WO92/15195 | 9/1992 | WIPO . |
| WO92/16637 | 10/1992 | WIPO . |

OTHER PUBLICATIONS

L. Carbonell et al, "Synthesis of a Gene Coding for an Insect–Specific Scorpion Neurotoxin and Attempts to Express its Using Baculovirus Vectors", *Gene*, 73 :409–418 (Jan., 1988).

L. Stewart et al, "Construction of an Improved Baculovirus Insecticide Containing an Insect–Specific Toxin Gene", *Nature*, 352:85–88 (Jul. 4, 1991).

S. Maeda et al, "Insecticidal Effects of an Insect–Specific Neurotoxin Expressed by a Recombinant Baculovirus", *Virology*, 184:777–780 (Oct., 1991).

G. Quistad et al, "Paralytic and Insecticidal Toxins from the Funnel Web Spider, *Hololena Curta*", *Toxicon*, 29(3):329–336 (1991).

C. Geren, "Neurotoxins and Necrotoxins of Spider Venoms", *J. Toxicol.–Toxin Reviews*, 5(2):161–170 (1986) [Geren I].

D. Sheumack et al, "Complete Amino Acid Sequence of a New Type of Lethal Neurotoxin from the Venon of the Funnel-Web Spider *Atrax Robustus*", *FEBS Letter*, 181(1):154–156 (Feb. 1985) [Sheumack I].

N. Frontali et al, "Purification from Black Widow Spider Venom of a Protein Factor Causing the Depletion of Synaptic Vesicles at Neuromuscular Junctions", *J. Cell Biol.*, 68:462–479 (1976).

(List continued on next page.)

*Primary Examiner*—Robert A. Wax
*Assistant Examiner*—Kawai Lau
*Attorney, Agent, or Firm*—Melissa A. Shaw

[57] ABSTRACT

The invention relates to toxins from venom of Australian funnel web spider species. Eight toxins are specifically exemplified. The toxins have a molecular weight of approximately 4000 amu., containing 36–37 amino acids, and are capable of forming 3 intrachain disulphide bridges. Polynucleotides which encode the toxins, insect viruses and plants which express the toxins and variants of the toxins are also included.

8 Claims, 18 Drawing Sheets

CLUSTAL V MULTIPLE SEQUENCE ALIGNMENT

```
a
1.  IN-1    S-TCTPTDQPCPYHESCCSGSCTYKANENGNQVKRCD
2.  IN-2    SPTCIPTGQPCPYNENCCSQSCTYKANENGNQVKRCD
3.  IN-3    SSTCIRTDQPCPYNESCCSGSCTYKANENGNQVKRCD
5.  V-1     SPTCIPSGQPCPYNENCCSQSCTFKENENGNTVKRCD
4.  MR-1    SSVCIPSGQPCPYNEHCCSGSCTYKENENGNTVQRCD
6.  F-1a    SPTCTGADRPCAACCPCCPGTSCKGPEPNGVSYCRND
7.  F-1a    SPTCTGADRPCAACCPCCPGTSCKGPEPNGVSYCRN
8.  F-1b    SPTCIRSGQPCPYNENCCSQSCTFKTNENGNTVKRCD
``` a SEQ ID No.

OTHER PUBLICATIONS

K. Hagiwara et al, "Complete Amino Acid Sequence of a New Type of Neurotoxin from the Venom of the Spider, *Agelena Opulenta*", *Biomed. Res.*, 11(3):181–186 (1990).

N. Zilberberg et al, "The cDNA Sequence of a Depressant Insect Selective Neurotoxin from the Scorpion *Buthotus Judaicus*", *Toxicon*, 29(9):1155–1158 (1991).

E. Loret et al, "Neurotoxins Active on Insects: Amino Acid Sequences, Chemical Modifications, and Secondary Structure Estimation by Cirular Dichroism of Toxins from the Scorpion *Androctonus australis* Hector", *Biochem.*, 29:1492–1501 (1990).

A. Stapleton et al, "Curtatoxins–Neurotoxic Insecticidal Polypeptides Isolated from the Funnel–Web Spider *Hololena Curta*", *J. Biol. Chem.*, 265(4):2054–2059 (Feb. 1990).

S. Sutherland, "Antivenom to the Venom of the Male Sydney Funnel–Web Spider *Atrax Robustus*", *Med. J. Aust.*, 2:437–441 (Oct. 18, 1980).

D. Sheumack et al, "A Comparative Study of Properties and Toxic Constituents of Funnel Web Spider (Atrax) Venoms", *Comp. Biochem. Physiol.*, 78C(1):55–68 (1984) [Sheumack II].

J. Houmard et al, "Staphylococcal Protease: A Proteolytic Enzyme Specific for Glutamoyl Bonds", *Proc. Natl. Acad. Sci. USA*, 69(12):3506–3509 (Dec. 1972).

M. Brown et al, "Amino acid Sequence of Versutoxin, a Lethal Neurotoxin from the Venom of the Funnel–Web Spider *Atrax versutus*", *Biochem. J.*, 250:401–405 (1988).

M. Adams et al, "omega–Agatoxins: Novel Calcium Channel Antagonists of Two Subtypes from Funnel Web Spider (*Agelenopsis aperta*) Venom", *J. Biol. Chem.*, 265(2):861–867 (Jan. 15, 1990).

W. Skinner et al, "Purification and Characterization of Two Classes of Neurotoxins from the Funnel Web Spider, *Agelenopsis aperta*", *J. Biol. Chem.*, 264(4):2150–2155 (Feb. 1989).

C. Bowers et al, "Identification and Purification of an Irreversible Presynaptic Neurotoxin from the Venom of the Spider *Hololena curta*", *Proc. Natl. Acad. Sci. USA*, 84:3506–3510 (May 1987).

W. Branton et al, "Neurotoxins from Plectreurys Spider Venom are Potent Presynaptic Blockers in Drosophila", *J. Neuroscience*, 7(12):4195–4200 (Dec. 1987).

D. Ross et al, "Peptide Toxins from Arthropod Venoms Disrupt Feeding and Utilization of Diet in the Cotton Bollworm", *Insect Neurochemistry and Neurophysiology*, pp. 401–404, eds. A. B. Borkovec et al, The Humana Press, Clifton, NJ (1986).

D. Quicke, "Spiders Bite their Way Towards Safer Insecticides", *New Scientist*, pp. 38–41 (Nov. 26, 1988) [Quicke I].

C. Kopeyan et al, "Primary Structure of Scorpion Anti–Insect Toxins Isolated from the Venom of *Leiurus quinquestriatus quinquestriatus*", *FEBS Letters*, 261(2):423–426 (Feb. 1990).

D. Sheumack et al, "Complete Amino Acid Sequence of a New Type of Lethal Neurotoxin from the Venom of the Funnel–Web Spider *Atrax robustus*", Abstract No. 181020z, *Chemical Abstracts*, 102(21):226 (May 27, 1985) [Sheumack III].

D. Quicke et al, "Spider Toxins as Lead Structures for Novel Pesticides", in *Safer Insecticides–Development and Use*, pp. 385–394, ed. E. Hodgson et al, (1990) [Quicke II].

R. Teakle et al, "*Heliothis Punctiger* Wallengren", in *Handbook of Insect Rearing*, vol. 2, ed. Singh and Moore, Elsevier Science, Amsterdam (1985).

M. O'Shea, "Neuropeptides in Insects: Possible Leads to New Control Methods", in *Approaches to New Leads for Insecticides*, ed. von Keyserlingk Jager and von Szczepanski Spring Verlag, Bellin, pp. 133–151 (1985).

D. Finney, "Estimation of the Median Effective Dose", in *Probit Analysis*, 34d ed. Cambridge University Press, pp. 20–31 (1971).

R. Gregson et al, "Isolation and Characterization of a Protein Neurotoxin from the Venom Glands of the Fennel–Web Spider (*Atrax Robustus*)", *Comp. Biochem. Physiol.*, 74C(1):125–132 (1983).

M. Gray et al, "Venoms of Dipluridae", *Handbuch der Experimentellen Pharmakologie*, vol. 48, pp. 132–133 (1978).

Geren et al, "Insect Poisons, Allergens, and Other Invertebrate Venoms", in *Handbook of Natural Toxins*, 2:463–464 (1984) [Geren II].

P. Usherwood, "The Action of Spider Toxins on the Insect Nerve–Muscle System", in *Approaches to New Leads for Insecticides*, pp. 71–79, ed. von Keyserlingk, Jager and von–Szczepanski, Springer Verlag, Berlin (1985).

In1

NH$_2$-SER THR CYS THR PRO THR ASP GLN PRO CYS PRO TYR HIS
GLU SER CYS CYS SER GLY SER CYS THR TYR LYS ALA ASN GLU ASN
GLY ASN GLN VAL LYS ARG CYS ASP-NH$_2$     (SEQ ID No 1)

In2

NH$_2$-SER PRO THR CYS ILE PRO THR GLY GLN PRO CYS PRO TYR
ASN GLU ASN CYS CYS SER GLN SER CYS THR TYR LYS ALA ASN GLU
ASN GLY ASN GLN VAL LYS ARG CYS ASP-NH$_2$     (SEQ ID No 2)

In3

NH$_2$-SER SER THR CYS ILE ARG THR ASP GLN PRO CYS PRO TYR
ASN GLU SER CYS CYS SER GLY SER CYS THR TYR LYS ALA ASN GLU
ASN GLY ASN GLN VAL LYS ARG CYS ASP-NH$_2$     (SEQ ID No 3)

MR1

NH$_2$-SER SER VAL CYS ILE PRO SER GLY GLN PRO CYS PRO TYR
ASN GLU HIS CYS CYS SER GLY SER CYS THR TYR LYS GLU ASN GLU
ASN GLY ASN THR VAL GLN ARG CYS$^3$ ASP-NH$_2$ (SEQ ID No 4)

VI

NH$_2$-SER PRO THR CYS ILE PRO SER GLY GLN PRO CYS PRO TYR
ASN GLU ASN CYS CYS SER GLN SER CYS THR PHE LYS GLU ASN GLU
ASN GLY ASN THR VAL LYS ARG CYS ASP-NH$_2$     (SEQ ID No 5)

FIG. 5

F1a  (SEQ ID No 6)

NH2-SER PRO THR CYS THR GLY ALA ASP ARG PRO CYS ALA
ALA CYS CYS PRO CYS CYS PRO GLY THR SER CYS LYS GLY
PRO GLU PRO ASN GLY VAL SER TYR CYS ARG ASN ASP-NH2

F1a  (SEQ ID No 7)

NH2-SER PRO THR CYS THR GLY ALA ASP ARG PRO CYS ALA
ALA CYS CYS PRO CYS CYS PRO GLY THR SER CYS LYS GLY
PRO GLU PRO ASN GLY VAL SER TYR CYS ARG ASN-NH2

F1b  (SEQ ID No 8)

NH2-SER PRO THR CYS ILE ARG SER GLY GLN PRO CYS PRO TYR
ASN GLU ASN CYS CYS SER GLN SER CYS THR PHE LYS THR ASN
GLU ASN GLY ASN THR VAL LYS ARG CYS ASP-NH2

FIG. 15

CLUSTAL V MULTIPLE SEQUENCE ALIGNMENT

```
a 1. IN-1    S-TCTPTDQPCPYHESCCSGSCTYKANENGNQVKRCD
  2. IN-2    SPTCIPTGQPCPYNENCCSQSCTYKANENGNQVKRCD
  3. IN-3    SSTCIRTDQPCPYNESCCSGSCTYKANENGNQVKRCD
  5. V-1     SPTCIPSGQPCPYNENCCSQSCTFKENENGNTVKRCD
  4. MR-1    SSVCIPSGQPCPYNEHCCSGSCTYKENENGNTVQRCD
  6. F-1a    SPTCTGADRPCAACCPCCPGTSCKGPEPNGVSYCRND
  7. F-1a    SPTCTGADRPCAACCPCCPGTSCKGPEPNGVSYCRN
  8. F-1b    SPTCIRSGQPCPYNENCCSQSCTFKTNENGNTVKRCD
```

FIG. 16 a SEQ ID No.

CLUSTAL V MULTIPLE SEQUENCE ALIGNMENT

```
A          REF
 1. IN-1         STCTPTDQPCPYHESCCSGSCTY---------------------KANENGNQVKRCD----
 2. IN-2         SPTCIPTGQPCPYNENCCSQSCT----------------------YKANENGNQVKRCD----
 3. IN-3         SSTCIRTDQPCPYNESCCSGSCT----------------------YKANENGNQVKRCD----
 5. V-1          SPTCIPSGQPCPYNENCCSQSCT----------------------FKENENGNTVKRCD----
 4. MR-1         SSVCIPSGQPCPYNEHCCSGSCT----------------------YKENENGNTVQRCD----
 6. F-1a         SPTCTGADRPCAACCPCCPGTSC----------------------KGPEPNGVSYCRND----
 8. F-1b         SPTCIRSGQPCPYNENCCSQSCT----------------------FKTNENGNTVKRCD----
13. U-aga-1    6 ECVPENGHCRDWYDECCEGFYCSCRQPPKCICRNNN-----------------------------
14. U-AGA-2      ECATKNKRCADWAGPWCCDGLYCSCRSYPGCMCRPSS-----------------------------
15. U-AGA-3      ADCVGDGQRCADWAGPYCCSGYYCSCRSMPYCRCRSDS----------------------------
16. U-AGA-4      ACVGENQQCADWAGPHCCDGYYCTCRYFPKCICRNNN-----------------------------
17. U-AGA-5      ACVGENKQCADWAGPHCCDGYYCTCRYFPKCICRNNN-----------------------------
18. U-AGA-6      DCVGESQQCADWAGPHCCDGYYCTCRYFPKCICVNNN-----------------------------
19. CT-1      18 SCVGEYGRCRSAYEDCCDGYYCNCSQPPYCLLCRNNN-----------------------------
20. CT-3      19 ADCVGDGQKCADWFGPYCCSGYYCSCRSMPYCRCRSDS----------------------------
21. AAHIT       KKNGYAVDSSGKAPECLLSNYCNNQCTKVHYADKGYCCLLSCYCFGLNDDKKVLEISDTRKSYCDTTIIN
22. AAHIT1      KKNGYAVDSSGKAPECLLSNYCNNECTKVHYADKGYCCLLSCYCFGLNDDKKVLEISDTRKSYCDTTIIN
23. AAHIT2      KKDGYAVDSSGKAPECLLSNYCYNECTKVYVHYADKGYCCLLSCYCFGLNDDKKVLEISDTRKSYCDTPIIN
``` a SEQ ID No.

FIG. 17

CLUSTAL V MULTIPLE SEQUENCE ALIGNMENT

```
a   REF                          ST------------CTPTDQPCPYHESCCSGSCTYK----------ANENGNQVKRCD-
1.  IN-1                         SP------------TCIPTGQPCPYNENCCSCCSGSCTY-----------KANENGNQVKRCD
2.  IN-2                         SS------------TCIRTDQPCPYNESCCSGSCTY-----------KANENGNQVKRCD
3.  IN-3                         SP------------TCIPSGQPCPYNENCCSQSCTF-----------KENENGNTVKRCD
5.  V-1                          SS------------VCIPSGQPCPYNEHCCSGSCTY-----------KENENGNTVQRCD
4.  MR-1                         SP------------TCTGADRPCAACCPCCPGTSCK-----------GPEPNGVSYCRND
6.  F-Ia                         SP------------TCIRSGQPCPYNENCCSQSCTF-----------KTNENGNTVKRCD
8.  F-Ib                         ALPLSGEYEPCVRPRKCCKPGLVCNKQQICVDPK-----------
24. SmpIT2                       DGYIRKRDGCKLSCLFGNEGCNKECKSYGGSYGYCWTWGLACWCEGLPDEKTWKSETNTCG
25. LqqIT2                       DGYIRKKDGCKVSCIIGNEGCRKECVAHGGSFGYCWTWGLACWCENLPDAVTWKSSTNTCG
26. BjIT2 a SEQ ID No.
```

FIG. 18

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Atrax infensus ( i x ) FEATURE:
        ( A ) NAME/KEY: Modified-site
        ( B ) LOCATION: 36
        ( D ) OTHER INFORMATION: /label=a
          / note= "this site may be amidated without loss of biological activity"

( x i ) SEQUENCE DESCRIPTION: SEQ ID NO:1:

```
Ser Thr Cys Thr Pro Thr Asp Gln Pro Cys Pro Tyr His Glu Ser Cys
1               5                   10                  15

Cys Ser Gly Ser Cys Thr Tyr Lys Ala Asn Glu Asn Gly Asn Gln Val
            20              25                  30

Lys Arg Cys Asp
        35
```

( 2 ) INFORMATION FOR SEQ ID NO:2:

( i ) SEQUENCE CHARACTERISTICS:
        ( A ) LENGTH: 37 amino acids
        ( B ) TYPE: amino acid (D) TOPOLOGY: linear (ii) MOLECULE TYPE: protein (iii) HYPOTHETICAL: NO (iv) ANTI-SENSE: NO (vi) ORIGINAL SOURCE:
 (A) ORGANISM: Atrax infensus (ix) FEATURE:
 (A) NAME/KEY: Modified-site
 (B) LOCATION: 37
 (D) OTHER INFORMATION: /label=a
  / note=

( i x ) FEATURE:
    ( A ) NAME/KEY: Modified-site
    ( B ) LOCATION: 37
    ( D ) OTHER INFORMATION: /label=a
        / note= "this site may be amidated without loss of biological activity"

( x i ) SEQUENCE DESCRIPTION: SEQ ID NO:4:

```
Ser Ser Val Cys Ile Pro Ser Gly Gln Pro Cys Pro Tyr Asn Glu His
1               5                   10                  15
Cys Cys Ser Gly Ser Cys Thr Tyr Lys Glu Asn Glu Asn Gly Asn Thr
            20                  25                  30
Val Gln Arg Cys Asp
            35
```

( 2 ) INFORMATION FOR SEQ ID NO:5:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Hadronyche versutus ( i x ) FEATURE:
        ( A ) NAME/KEY: Modified-site
        ( B ) LOCATION: 37
        ( D ) OTHER INFORMATION: /label=a
            / note= "this site may be amidated without loss of biological activity"

( x i ) SEQUENCE DESCRIPTION: SEQ ID NO:5:

```
Ser Pro Thr Cys Ile Pro Ser Gly Gln Pro Cys Pro Tyr Asn Glu Asn
1               5                   10                  15
Cys Cys Ser Gln Ser Cys Thr Phe Lys Glu Asn Glu Asn Gly Asn Thr
            20                  25                  30
Val Lys Arg Cys Asp
            35
```

( 2 ) INFORMATION FOR SEQ ID NO:6:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Atrax formidabilis ( i x ) FEATURE:
        ( A ) NAME/KEY: Modified-site
        ( B ) LOCATION: 37
        ( D ) OTHER INFORMATION: /label=a
            / note= "this site may be amidated without loss of biological activity"

( x i ) SEQUENCE DESCRIPTION: SEQ ID NO:6:

```
Ser  Pro  Thr  Cys  Thr  Gly  Ala  Asp  Arg  Pro  Cys  Ala  Ala  Cys  Cys  Pro
1                   5                        10                       15

Cys  Cys  Pro  Gly  Thr  Ser  Cys  Lys  Gly  Pro  Glu  Pro  Asn  Gly  Val  Ser
               20                       25                       30

Tyr  Cys  Arg  Asn  Asp
               35
```

( 2 ) INFORMATION FOR SEQ ID NO:7:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Atrax formidabilis ( x i ) SEQUENCE DESCRIPTION: SEQ ID NO:7:

```
Ser  Pro  Thr  Cys  Thr  Gly  Ala  Asp  Arg  Pro  Cys  Ala  Ala  Cys  Cys  Pro
1                   5                        10                       15

Cys  Cys  Pro  Gly  Thr  Ser  Cys  Lys  Gly  Pro  Glu  Pro  Asn  Gly  Val  Ser
               20                       25                       30

Tyr  Cys  Arg  Asn
               35
```

( 2 ) INFORMATION FOR SEQ ID NO:8:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Atrax formidabilis ( i x ) FEATURE:
        ( A ) NAME/KEY: Modified-site
        ( B ) LOCATION: 37
        ( D ) OTHER INFORMATION: /label=a
            / note= "this site may be amidated without loss
            of biological activity"

( x i ) SEQUENCE DESCRIPTION: SEQ ID NO:8:

```
Ser  Pro  Thr  Cys  Ile  Arg  Ser  Gly  Gln  Pro  Cys  Pro  Tyr  Asn  Glu  Asn
1                   5                        10                       15

Cys  Cys  Ser  Gln  Ser  Cys  Thr  Phe  Lys  Thr  Asn  Glu  Asn  Gly  Asn  Thr
               20                       25                       30

Val  Lys  Arg  Cys  Asp
               35
```

( 2 ) INFORMATION FOR SEQ ID NO:9:

( i ) SEQUENCE CHARACTERISTICS:
        ( A ) LENGTH: 9 amino acids
        ( B ) TYPE: amino acid
        ( D ) TOPOLOGY: linear (i i) MOLECULE TYPE: peptide (i i i) HYPOTHETICAL: NO (i v) ANTI-SENSE: NO (v) FRAGMENT TYPE: C-terminal (v i) ORIGINAL SOURCE:
 (A) ORGANISM: Atrax infensus (x i) SEQUENCE DESCRIPTION: SEQ ID NO:9:

```
Asn Gly Asn Gln Val Lys Arg Cys Asp
1               5
```

(2) INFORMATION FOR SEQ ID NO:10:

(i) SEQUENCE CHARACTERISTICS:
  (A) LENGTH: 9 amino acids
  (B) TYPE: amino acid
  (D) TOPOLOGY: linear (i i) MOLECULE TYPE: peptide (i i i) HYPOTHETICAL: NO (i v) ANTI-SENSE: NO (v) FRAGMENT TYPE: C-terminal (v i) ORIGINAL SOURCE:
  (A) ORGANISM: Atrax infensus (i x) FEATURE:
  (A) NAME/KEY: Modified-site
  (B) LOCATION: 9
  (D) OTHER INFORMATION: /label=a
   / note= "this site correponding to the
   C-terminus of the parent molecule is amidated"

(x i) SEQUENCE DESCRIPTION: SEQ ID NO:10:

```
Asn Gly Asn Gln Val Lys Arg Cys Asp
1               5
```

(2) INFORMATION FOR SEQ ID NO:11:

(i) SEQUENCE CHARACTERISTICS:
  (A) LENGTH: 9 amino acids
  (B) TYPE: amino acid
  (D) TOPOLOGY: linear (i i) MOLECULE TYPE: peptide (i i i) HYPOTHETICAL: NO (i v) ANTI-SENSE: NO (v) FRAGMENT TYPE: C-terminal (v i) ORIGINAL SOURCE:
  (A) ORGANISM: Hadronyche versutus (i x) FEATURE:
  (A) NAME/KEY: Modified-site
  (B) LOCATION: 8
  (D) OTHER INFORMATION: /label=A
   / note= "this site is a CM derivative"

(x i) SEQUENCE DESCRIPTION: SEQ ID NO:11:

```
Asn Gly Asn Thr Val Lys Arg Cys Asp
1               5
```

(2) INFORMATION FOR SEQ ID NO:12:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
    ( A ) ORGANISM: Hadronyche versutus ( i x ) FEATURE:
    ( A ) NAME/KEY: Modified-site
    ( B ) LOCATION: order(4, 11)
    ( D ) OTHER INFORMATION: /label=a
        / note= "sites 4 and 11 are CM derivatives"

( x i ) SEQUENCE DESCRIPTION: SEQ ID NO:12:

```
Ser Pro Thr Cys Ile Pro Ser Gly Gln Pro Cys Pro Tyr Asn Glu
 1           5                  10                      15
```

( 2 ) INFORMATION FOR SEQ ID NO:13:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Agelenopsis aperta ( x i ) SEQUENCE DESCRIPTION: SEQ ID NO:13:

```
Glu Cys Val Pro Glu Asn Gly His Cys Arg Asp Trp Tyr Asp Glu Cys
 1           5                  10                      15

Cys Glu Gly Phe Tyr Cys Ser Cys Arg Gln Pro Pro Lys Cys Ile Cys
            20                  25                  30

Arg Asn Asn Asn
        35
```

( 2 ) INFORMATION FOR SEQ ID NO:14:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Agelenopsis aperta ( x i ) SEQUENCE DESCRIPTION: SEQ ID NO:14:

```
Glu Cys Ala Thr Lys Asn Lys Arg Cys Ala Asp Trp Ala Gly Pro Trp
 1           5                  10                      15

Cys Cys Asp Gly Leu Tyr Cys Ser Cys Arg Ser Tyr Pro Gly Cys Met
            20                  25                  30
```

Cys Arg Pro Ser Ser
         35

( 2 ) INFORMATION FOR SEQ ID NO:15:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Agelenopsis aperta ( x i ) SEQUENCE DESCRIPTION: SEQ ID NO:15:

Ala Asp Cys Val Gly Asp Gly Gln Arg Cys Ala Asp Trp Ala Gly Pro
1               5                   10                  15

Tyr Cys Cys Ser Gly Tyr Tyr Cys Ser Cys Arg Ser Met Pro Tyr Cys
                20                  25                  30

Arg Cys Arg Ser Asp Ser
         35

( 2 ) INFORMATION FOR SEQ ID NO:16:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Agelenopsis aperta ( x i ) SEQUENCE DESCRIPTION: SEQ ID NO:16:

Ala Cys Val Gly Glu Asn Gln Gln Cys Ala Asp Trp Ala Gly Pro His
1               5                   10                  15

Cys Cys Asp Gly Tyr Tyr Cys Thr Cys Arg Tyr Phe Pro Lys Cys Ile
                20                  25                  30

Cys Arg Asn Asn Asn
         35

( 2 ) INFORMATION FOR SEQ ID NO:17:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Agelenopsis aperta ( x i ) SEQUENCE DESCRIPTION: SEQ ID NO:17:

Ala Cys Val Gly Glu Asn Lys Gln Cys Ala Asp Trp Ala Gly Pro His
1               5                   10                  15

```
Cys Cys Asp Gly Tyr Tyr Cys Thr Cys Arg Tyr Phe Pro Lys Cys Ile
            20                  25                  30

Cys Arg Asn Asn Asn
        35
```

( 2 ) INFORMATION FOR SEQ ID NO:18:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Agelenopsis aperta ( x i ) SEQUENCE DESCRIPTION: SEQ ID NO:18:

```
Asp Cys Val Gly Glu Ser Gln Gln Cys Ala Asp Trp Ala Gly Pro His
1               5                   10                  15

Cys Cys Asp Gly Tyr Tyr Cys Thr Cys Arg Tyr Phe Pro Lys Cys Ile
            20                  25                  30

Cys Val Asn Asn Asn
        35
```

( 2 ) INFORMATION FOR SEQ ID NO:19:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Hololena curta ( x i ) SEQUENCE DESCRIPTION: SEQ ID NO:19:

```
Ser Cys Val Gly Glu Tyr Gly Arg Cys Arg Ser Ala Tyr Glu Asp Cys
1               5                   10                  15

Cys Asp Gly Tyr Tyr Cys Asn Cys Ser Gln Pro Pro Tyr Cys Leu Cys
            20                  25                  30

Arg Asn Asn Asn
        35
```

( 2 ) INFORMATION FOR SEQ ID NO:20:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Hololena curta (xi) SEQUENCE DESCRIPTION: SEQ ID NO:20:

| Ala | Asp | Cys | Val | Gly | Asp | Gly | Gln | Lys | Cys | Ala | Asp | Trp | Phe | Gly | Pro |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Tyr | Cys | Cys | Ser | Gly | Tyr | Tyr | Cys | Ser | Cys | Arg | Ser | Met | Pro | Tyr | Cys |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Arg | Cys | Arg | Ser | Asp | Ser |
|-----|-----|-----|-----|-----|-----|
|     |     | 35  |     |     |     |

(2) INFORMATION FOR SEQ ID NO:21:

(i) SEQUENCE CHARACTERISTICS:
      (A) LENGTH: 70 amino acids
      (B) TYPE: amino acid
      (D) TOPOLOGY: linear (ii) MOLECULE TYPE: protein (iii) HYPOTHETICAL: NO (iv) ANTI-SENSE: NO (vi) ORIGINAL SOURCE:
      (A) ORGANISM: Androctonus australis Hector (xi) SEQUENCE DESCRIPTION: SEQ ID NO:21:

| Lys | Lys | Asn | Gly | Tyr | Ala | Val | Asp | Ser | Ser | Gly | Lys | Ala | Pro | Glu | Cys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Leu | Ser | Asn | Tyr | Cys | Asn | Asn | Gln | Cys | Thr | Lys | Val | His | Tyr | Ala |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Asp | Lys | Gly | Tyr | Cys | Cys | Leu | Leu | Ser | Cys | Tyr | Cys | Phe | Gly | Leu | Asn |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Asp | Asp | Lys | Lys | Val | Leu | Glu | Ile | Ser | Asp | Thr | Arg | Lys | Ser | Tyr | Cys |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Asp | Thr | Thr | Ile | Ile | Asn |
|-----|-----|-----|-----|-----|-----|
| 65  |     |     |     |     | 70  |

(2) INFORMATION FOR SEQ ID NO:22:

(i) SEQUENCE CHARACTERISTICS:
      (A) LENGTH: 70 amino acids
      (B) TYPE: amino acid
      (D) TOPOLOGY: linear (ii) MOLECULE TYPE: protein (iii) HYPOTHETICAL: NO (iv) ANTI-SENSE: NO (vi) ORIGINAL SOURCE:
      (A) ORGANISM: Adroctonus australis Hector (xi) SEQUENCE DESCRIPTION: SEQ ID NO:22:

| Lys | Lys | Asn | Gly | Tyr | Ala | Val | Asp | Ser | Ser | Gly | Lys | Ala | Pro | Glu | Cys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Leu | Ser | Asn | Tyr | Cys | Asn | Asn | Glu | Cys | Thr | Lys | Val | His | Tyr | Ala |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Asp | Lys | Gly | Tyr | Cys | Cys | Leu | Leu | Ser | Cys | Tyr | Cys | Phe | Gly | Leu | Asn |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Asp | Asp | Lys | Lys | Val | Leu | Glu | Ile | Ser | Asp | Thr | Arg | Lys | Ser | Tyr | Cys |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Asp | Thr | Thr | Ile | Ile | Asn |
|-----|-----|-----|-----|-----|-----|
| 65  |     |     |     |     | 70  |

(2) INFORMATION FOR SEQ ID NO:23:

(i) SEQUENCE CHARACTERISTICS:
      (A) LENGTH: 70 amino acids
      (B) TYPE: amino acid
      (D) TOPOLOGY: linear (ii) MOLECULE TYPE: protein (iii) HYPOTHETICAL: NO (iv) ANTI-SENSE: NO (vi) ORIGINAL SOURCE:
      (A) ORGANISM: Androctonus australia Hector (xi) SEQUENCE DESCRIPTION: SEQ ID NO:23:

| Lys | Lys | Asp | Gly | Tyr | Ala | Val | Asp | Ser | Ser | Gly | Lys | Ala | Pro | Glu | Cys |
|---|---|---|---|---|---|---|---|---|---|---|---|---|---|---|---|
| 1 | | | | 5 | | | | | 10 | | | | | 15 | |

| Leu | Leu | Ser | Asn | Tyr | Cys | Tyr | Asn | Glu | Cys | Thr | Lys | Val | His | Tyr | Ala |
|---|---|---|---|---|---|---|---|---|---|---|---|---|---|---|---|
| | | | 20 | | | | | 25 | | | | | 30 | | |

| Asp | Lys | Gly | Tyr | Cys | Cys | Leu | Leu | Ser | Cys | Tyr | Cys | Phe | Gly | Leu | Asn |
|---|---|---|---|---|---|---|---|---|---|---|---|---|---|---|---|
| | | 35 | | | | | 40 | | | | | 45 | | | |

| Asp | Asp | Lys | Lys | Val | Leu | Glu | Ile | Ser | Asp | Thr | Arg | Lys | Ser | Tyr | Cys |
|---|---|---|---|---|---|---|---|---|---|---|---|---|---|---|---|
| | 50 | | | | | 55 | | | | | 60 | | | | |

| Asp | Thr | Pro | Ile | Ile | Asn |
|---|---|---|---|---|---|
| 65 | | | | | 70 |

(2) INFORMATION FOR SEQ ID NO:24:

(i) SEQUENCE CHARACTERISTICS:
      (A) LENGTH: 33 amino acids
      (B) TYPE: amino acid
      (D) TOPOLOGY: linear (ii) MOLECULE TYPE: protein (iii) HYPOTHETICAL: NO (iv) ANTI-SENSE: NO (vi) ORIGINAL SOURCE:
      (A) ORGANISM: Scorpio maurus palmatus (xi) SEQUENCE DESCRIPTION: SEQ ID NO:24:

| Ala | Leu | Pro | Leu | Ser | Gly | Glu | Tyr | Glu | Pro | Cys | Val | Arg | Pro | Arg | Lys |
|---|---|---|---|---|---|---|---|---|---|---|---|---|---|---|---|
| 1 | | | | 5 | | | | | 10 | | | | | 15 | |

| Cys | Lys | Pro | Gly | Leu | Val | Cys | Asn | Lys | Gln | Gln | Ile | Cys | Val | Asp | Pro |
|---|---|---|---|---|---|---|---|---|---|---|---|---|---|---|---|
| | | | 20 | | | | | 25 | | | | | 30 | | |

Lys (2) INFORMATION FOR SEQ ID NO:25:

(i) SEQUENCE CHARACTERISTICS:
      (A) LENGTH: 61 amino acids
      (B) TYPE: amino acid
      (D) TOPOLOGY: linear (ii) MOLECULE TYPE: protein (iii) HYPOTHETICAL: NO (iv) ANTI-SENSE: NO (vi) ORIGINAL SOURCE:
      (A) ORGANISM: Leiurus quinquestriatus quinquestriatus (xi) SEQUENCE DESCRIPTION: SEQ ID NO:25:

Asp Gly Tyr Ile Arg Lys Arg Asp Gly Cys Lys Leu Ser Cys Leu Phe

| 1 | | | | 5 | | | | | 10 | | | | | 15 | |
|---|---|---|---|---|---|---|---|---|---|---|---|---|---|---|---|
| Gly | Asn | Glu | Gly | Cys | Asn | Lys | Glu | Cys | Lys | Ser | Tyr | Gly | Gly | Ser | Tyr |
| | | | 20 | | | | | 25 | | | | | 30 | | |
| Gly | Tyr | Cys | Trp | Thr | Trp | Gly | Leu | Ala | Cys | Trp | Cys | Glu | Gly | Leu | Pro |
| | | 35 | | | | | 40 | | | | | 45 | | | |
| Asp | Glu | Lys | Thr | Trp | Lys | Ser | Glu | Thr | Asn | Thr | Cys | Gly | | | |
| | 50 | | | | | 55 | | | | | 60 | | | | |

( 2 ) INFORMATION FOR SEQ ID NO:26:

( i ) SEQUENCE CHARACTERISTICS:
        ( A ) LENGTH: 61 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Buthotus judaicus ( x i ) SEQUENCE DESCRIPTION: SEQ ID NO:26:

| Asp | Gly | Tyr | Ile | Arg | Lys | Lys | Asp | Gly | Cys | Lys | Val | Ser | Cys | Ile | Ile |
|---|---|---|---|---|---|---|---|---|---|---|---|---|---|---|---|
| 1 | | | | 5 | | | | | 10 | | | | | 15 | |
| Gly | Asn | Glu | Gly | Cys | Arg | Lys | Glu | Cys | Val | Ala | His | Gly | Gly | Ser | Phe |
| | | | 20 | | | | | 25 | | | | | 30 | | |
| Gly | Tyr | Cys | Trp | Thr | Trp | Gly | Leu | Ala | Cys | Trp | Cys | Glu | Asn | Leu | Pro |
| | | 35 | | | | | 40 | | | | | 45 | | | |
| Asp | Ala | Val | Thr | Trp | Lys | Ser | Ser | Thr | Asn | Thr | Cys | Gly | | | |
| | 50 | | | | | 55 | | | | | 60 | | | | |

INSECTICIDAL TOXINS DERIVED FROM FUNNEL WEB (ATRAX OR HADRONYCHE) SPIDERS

This application is a continuation of application Ser. No. 08/256,933, filed as PCT/AU93/00039 Jan. 29, 1993 published as WO93/15108 now abandoned.

TECHNICAL FIELD

The present invention relates to the isolation and characterization of toxins suitable for use as insecticides.

Toxins active against insects, and in particular against species of Heliothis, are of particular interest because of the major economic importance of this insect. The identification of new compounds provides a base for the development of an alternative class of agricultural insecticides.

BACKGROUND ART

The need for an alternative to existing chemical insect control measures is becoming increasingly apparent as insect resistance to pesticides increases, unintended effects of pesticides are acknowledged and environmental considerations generally achieve more prominence. The consequent cost of control measures, and losses suffered, makes some previously profitable agricultural industries non-viable.

Recently, there has been a renewal of interest in the pharmacological and chemical examination of venoms, particularly spider venoms, and the toxins they contain.

Some authors[1,2,3] have proposed development of insecticidal materials from spider venoms as a general proposition, based on the ability of some spider venoms to kill certain insects, or in reference to low molecular weight reversibly-acting polyamine toxins.

The moth Heliothis armigera is the major pest of field crops in Australia. H. armigera is a migratory moth, the larvae of which feed on a wide range of agricultural crops. The genus Heliothis has worldwide distribution. H. zea occurs in the Americas from Canada to Uruguay. H. armigera, which is very similar, is found in southern Europe, Africa, the Near and Middle East, the Far East, Australia, New Zealand and many of the Pacific Islands. In Australia, *H. armigera* infests and causes serious damage to cotton, tobacco, tomato, green bean, sweet corn, lucerne, soybean, sorghum, field pea, linseed, safflower, rapeseed, sunflower and field lupins. However, in terms of costs of *H. armigera* and losses due to it, cotton is by far the most important of these crops.

DESCRIPTION OF THE INVENTION

The present inventors have isolated a homologous series of novel insecticidal peptides from Australian funnel web spiders (genera Atrax and Hadronyche), of relatively low molecular weight (approx. 4000 a.m.u.), and have demonstrated irreversible toxicity for these peptides when injected into specimens of *Heliothis armigera*. It is expected that these peptides would exhibit toxicity against a number of other insect species. The toxins have been shown to be lethal or toxic by injection to pests such as species of locust, cockroach, blowfly and beetle.

The toxins isolated and characterised show only limited similarity to previously reported insect-active toxins. For example, insect specific toxins isolated from Plectreurys species[4], which elute chromatographically in a similar acetonitrile concentration and are single chain toxins, have an estimated molecular weight of about 7000 a.m.u., which is much greater than the approximately 4000 a.m.u. mass of the toxins of the invention. Active compounds originally isolated from Hololena species[5], in contrast, are considered to be composed of two subunits with a total molecular mass of around 16000 a.m.u. although subsequent reports describe the isolation of single chain insect toxins from this species[18]. They are believed to act via a presynaptic calcium channel blocking mechanism.

Of the published data, the μ-agatoxins from Agelenopsis venom[6] are most similar to the toxins of the present invention, being of similar size (36–38 residues, molecular weight about 4200 a.m.u.) and single chain toxins. Sequence homology between the two sets of toxins is minimal, as is the case also for the ω-agatoxins[7] (7500–11000 a.m.u.).

The insect active toxins of the present invention are a homologous group quite distinct from the mammalian toxins previously isolated from Australian funnel web spiders[8,9], and consequently no bioactivity would be expected in mammalian systems. In fact, no activity was found when 500 pmol and 400 pmol of toxins In2 and In3 respectively were injected into the tail vein of a mature mouse, and V1 has been shown not to be toxic in newborn mice.

According to a first embodiment of the present invention there is provided a toxin which is a polypeptide having a relative molecular mass of approximately 4000 a.m.u., consisting of 36–37 amino acid residues and being capable of forming 3 intrachain disulphide bridges which toxin is toxic for larval and/or adult insects. Typically this toxicity is demonstrated by the exhibition of abnormal movements and failure of the larva to pupate at the usual time with eventual death.

The toxin of the invention as herein defined excludes the toxin as it occurs in its natural environment. The toxin isolated in form suitable for sequencing generally has a purity of the order of about 95% although it is readily apparent that this level of purity is not required for a commercially useful product.

The invention encompasses the toxins in both carboxyamidated and free acid forms.

Preferred toxins of the present invention are In1 (SEQ ID NO:1), In2 (SEQ ID NO:2), In3 (SEQ ID NO:3), MR1 (SEQ ID NO:4), V1 (SEQ ID NO:5), F1a (SEQ ID NO:6 & SEQ ID NO:7) and F1b (SEQ ID NO:8) as herein defined.

The toxins of the present invention can be isolated from spider venom.

They may also be synthesized, chemically or by recombinant techniques from the isolated gene encoding the toxin or its preprotein or from a synthetic or cDNA copy of the gene.

Where recombinant techniques are used for the preparation of toxins of the invention, the toxins can be prepared by constructing DNA probes coding for amino acid sequences of the toxins of the invention.

These probes can then be used to isolate the genes coding for toxin preproteins from DNA from spider cells, or prepared as cDNA from spider cell mRNA, cloned into suitable vectors, in a DNA library. Such libraries are prepared by standard techniques. The isolated preprotein genes can be sequenced by standard methods and inserted into the genome, for instance, of an appropriate insect virus, such as a baculovirus, so that the corresponding toxin preproteins are expressed as late proteins during infection of the insect and/or larvae by the virus. Alternatively, plant lines may be engineered to express the toxin genes. Methods suitable for incorporating the toxin genes into insect virus or plant hosts are taught in Australian Patent Application No 46881/89 by Ciba Geigy AG, relating to scorpion toxins unrelated to the toxins of this invention. Further, synthetic toxin genes can be constructed by standard DNA synthesis techniques and preferably using knowledge of insect virus or plant gene codon usage and insect virus or plant consensus start sequences, can be inserted into insect virus or plant expression systems. Polynucleotide sequences whether isolated from natural sources or synthesized and encoding the toxins of the invention are also within the scope of the present invention.

Carboxyamidation of the recombinant protein may be achieved post-translationally.

The invention further provides insect viruses and plant species engineered to express the toxins of this invention. Typically, the insect viruses and plant species will express the toxins of the invention free from other funnel-web spider proteins.

The invention also provides variants of these toxins wherein a variant is a polypeptide which corresponds to or comprises a portion of a polypeptide toxin of the invention or is a polypeptide which has a relative molecular mass of approximately 4000 a.m.u., consists of 36–37 residues and is capable of forming 3 intrachain disulphide bridges, is toxic for insects and/or their larvae and is homologous to a toxin of the invention. For the purposes of this description "homology" between two peptide sequences connotes a likeness short of identity, indicative of a derivation of the first sequence from the second. In particular, a polypeptide is "homologous" to a toxin of the invention if a comparison of amino-acid sequences between the polypeptide and the toxin reveals an identity of greater than about 70%. Such a sequence comparison can be performed via known algorithms, such as the one described by Lipman and Pearson[10] which are readily implemented by computer.

The homologous polypeptides can be produced, in accordance with the present invention, by conventional site-directed mutagenesis, which is one avenue for routinely identifying residues of the molecule that can be modified without rendering the resulting polypeptide biologically inactive, or by chemical synthesis.

Those variants which correspond to or comprise a portion of a toxin of the invention without being coincident with a toxin of the invention, within the scope of the invention, are those molecules which retain the toxicity of the toxin for insects and/or their larvae.

These variants may be prepared synthetically by peptide synthesis techniques, recombinantly or by cleavage from an isolated toxin of the invention.

The variants of the invention may be assayed for toxicity following the procedures outlined for the toxins of the invention.

Polynucleotides encoding variants of the toxins of the present invention are also within the scope of this invention. Insect viruses and plants may be engineered to express the variants in a manner analogous to that set forth for the toxins themselves, and these insect viruses and plants also form part of the present invention.

According to a second embodiment of the present invention there is provided an insecticidal composition for delivering a toxin or a toxin variant of the first embodiment. For instance where the toxin or variant can be expressed by an insect virus as a late protein, the virus encoding the toxin or variant can be applied to the crop to be protected. The virus may be formulated in an agriculturally acceptable carrier, diluent and/or excipient. Suitable agents include those routinely used in agricultural formulations and include aqueous carriers. The compositions are formulated in accordance with standard agricultural procedures. Suitable viruses include baculoviruses.

Alternatively the crop itself of another appropriate plant may be engineered to express the toxin.

According to a third embodiment of the present invention there is provided a method for controlling infestation of crops by insect pests which method comprises treating the crops or the insects and/or their larvae with a composition of the second embodiment. The toxin or variant may be applied in the form of an insect virus engineered to be capable of expressing the toxin or variant as a late protein. The insects and/or their larvae may be treated with the composition, for example, by attracting the insects to the composition with an attractant.

Alternatively, the method may comprise providing a crop or plant engineered to express the toxin. Crops for which this approach would be useful include cotton, tobacco, tomato, green bean, sweet corn, lucerne, soybean, sorghum, field pea, linseed, safflower, rapeseed, sunflower, and field lupins.

BRIEF DESCRIPTION OF THE DRAWINGS

FIG. 5 shows the amino acid sequences of toxins In1 (SEQ ID NO:1), In2 (SEQ ID NO:2), In3 (SEQ ID NO:3), MR1 (SEQ ID NO:4), V1 (SEQ ID NO:5) as obtained by gas. MR1 (SEQ ID No 4), V1 (SEQ ID No 5) as obtained by gas phase sequencing.

NOTES:

1. Underlined residues were also sequenced from *S. aureus* V8 protease digest.
2. Although structures are shown with amidated carboxy termini there is evidence for the carboxy terminus being the free acid in these toxins.
3. The final cysteine residue in MR1 is assumed from sequence homology. The first five such residues were detected as carboxymethyl derivatives during sequencing.

Figure 6:
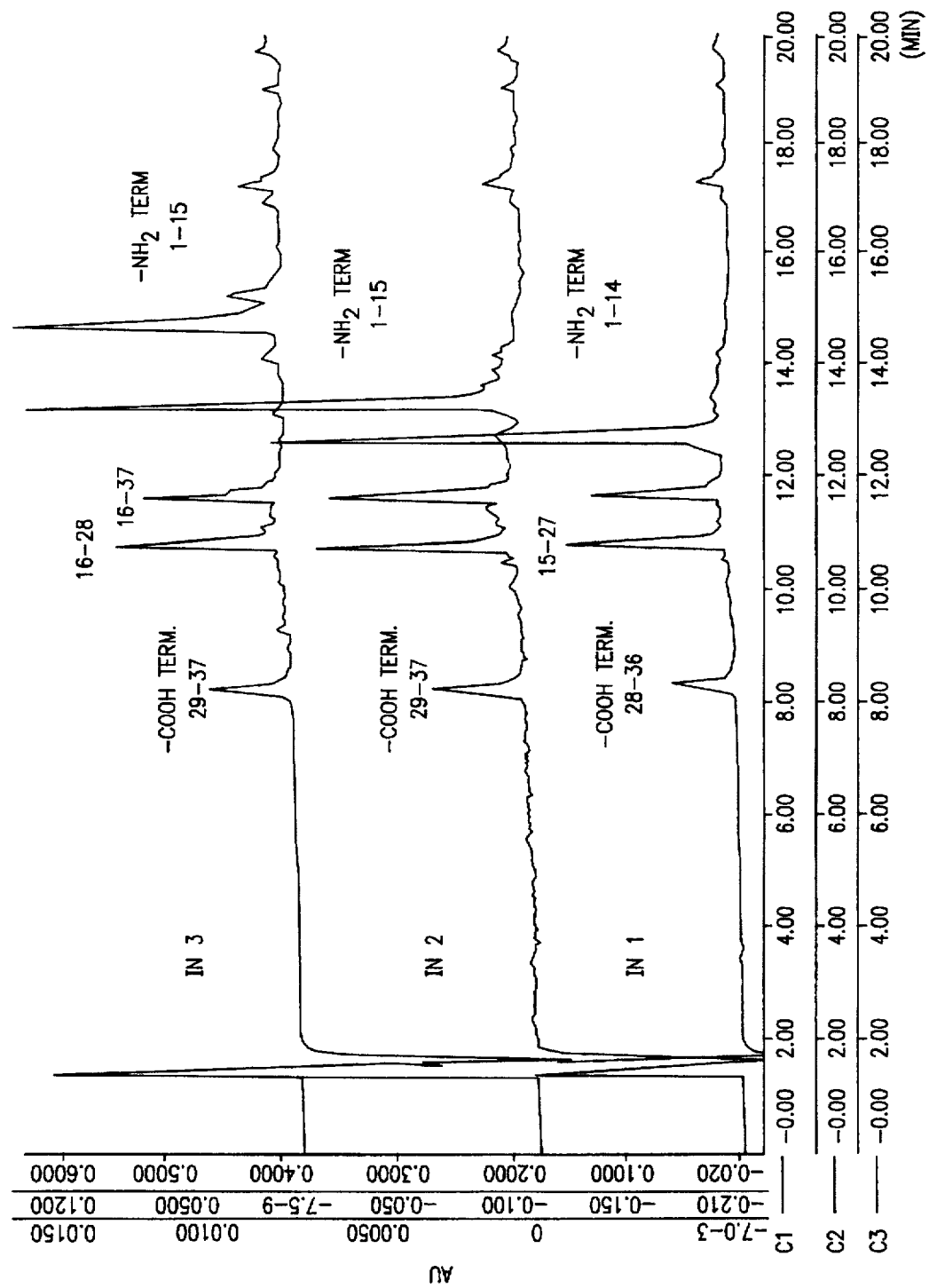

FIG. 6 shows the chromatographic profiles of *S. aureus* V8 protease digested In1 (SEQ ID NO:1), In2 (SEQ ID NO:2) and In3 (SEQ ID NO:3). The HPLC conditions are the same as in FIG. 1.

Figure 7:
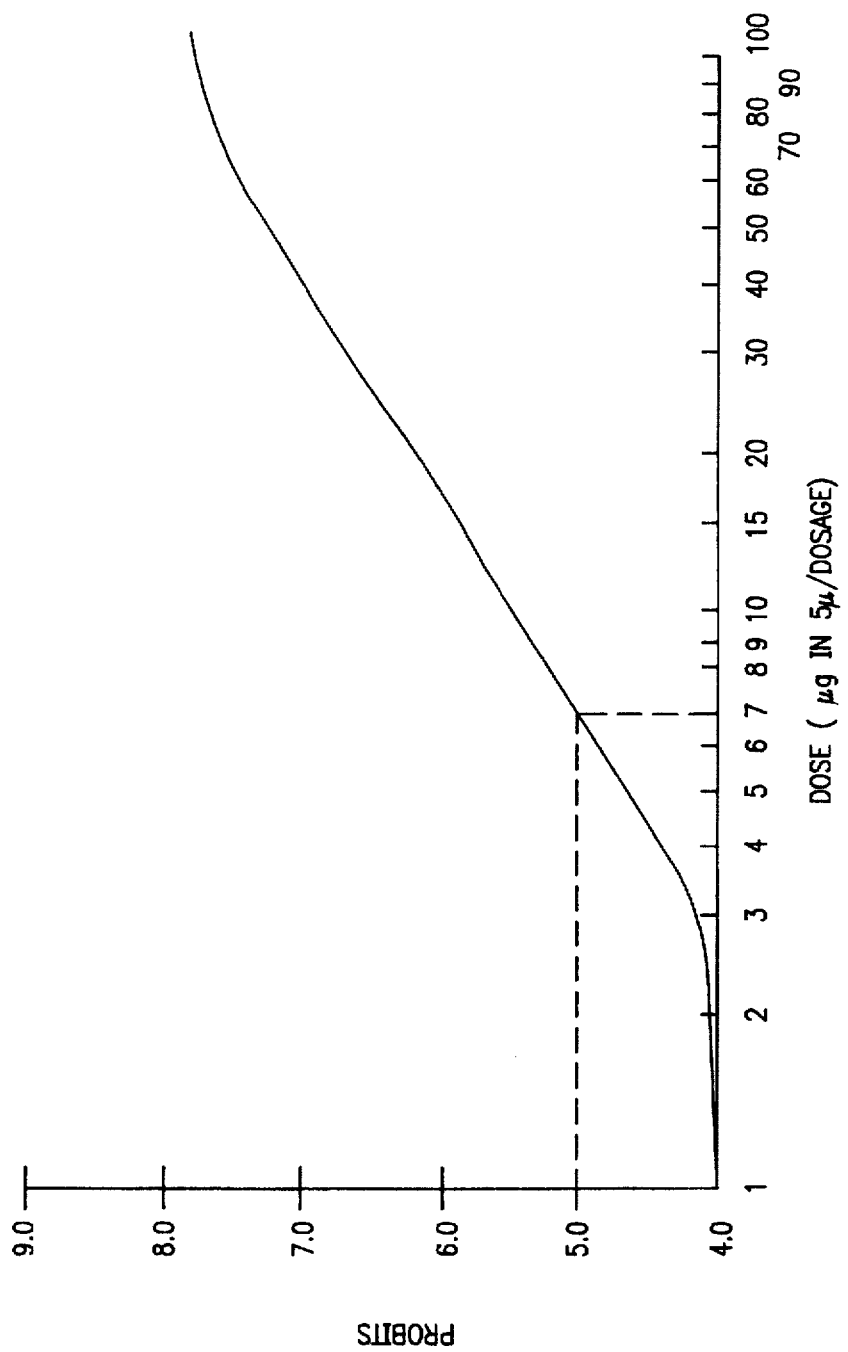

FIG. 7 shows the probit estimation of the effective dose (50%) for V1 toxin on Heliothis larvae. ED 50=7 micrograms/larva.

Figure 8:
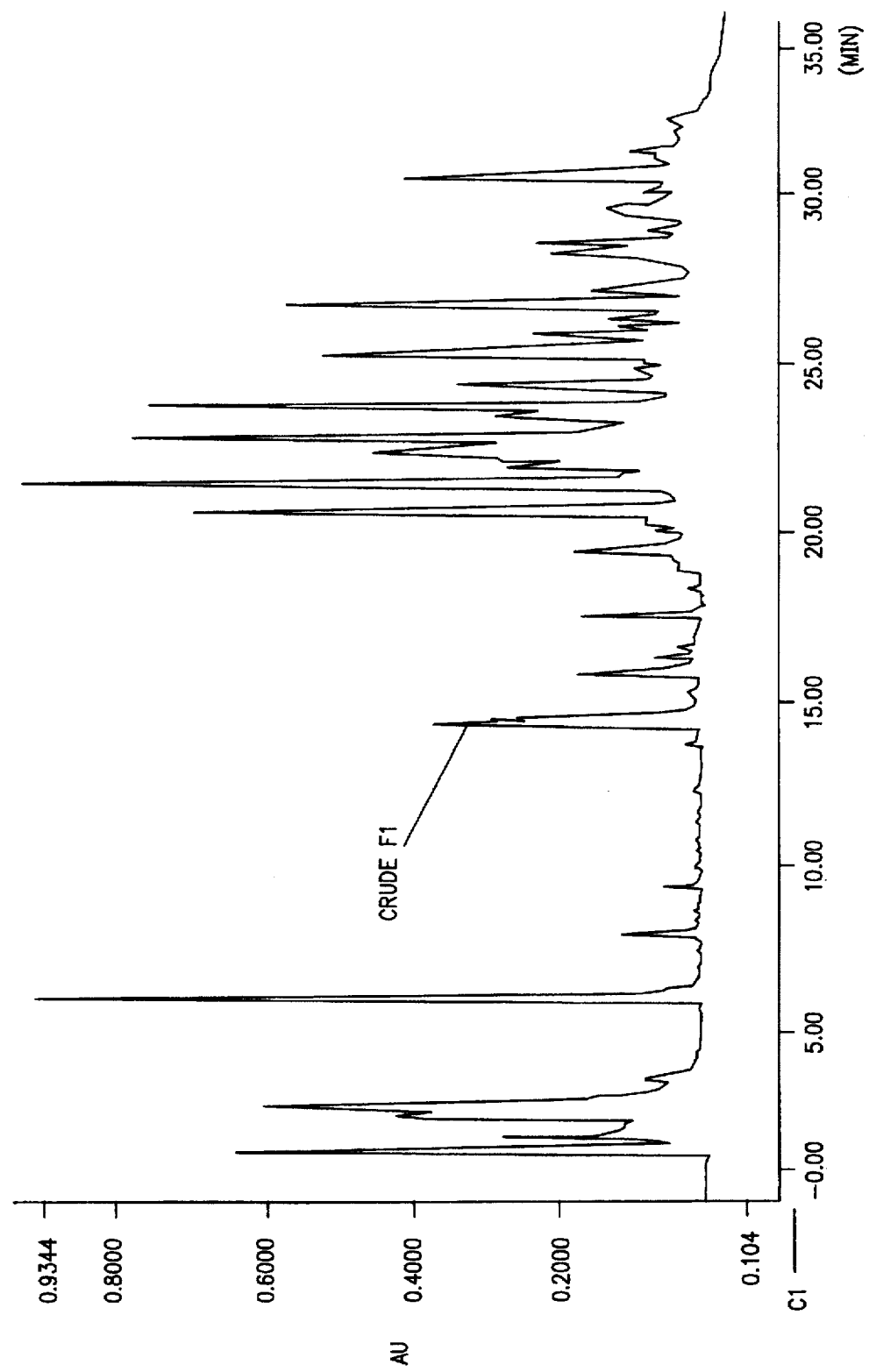
Figure 9:
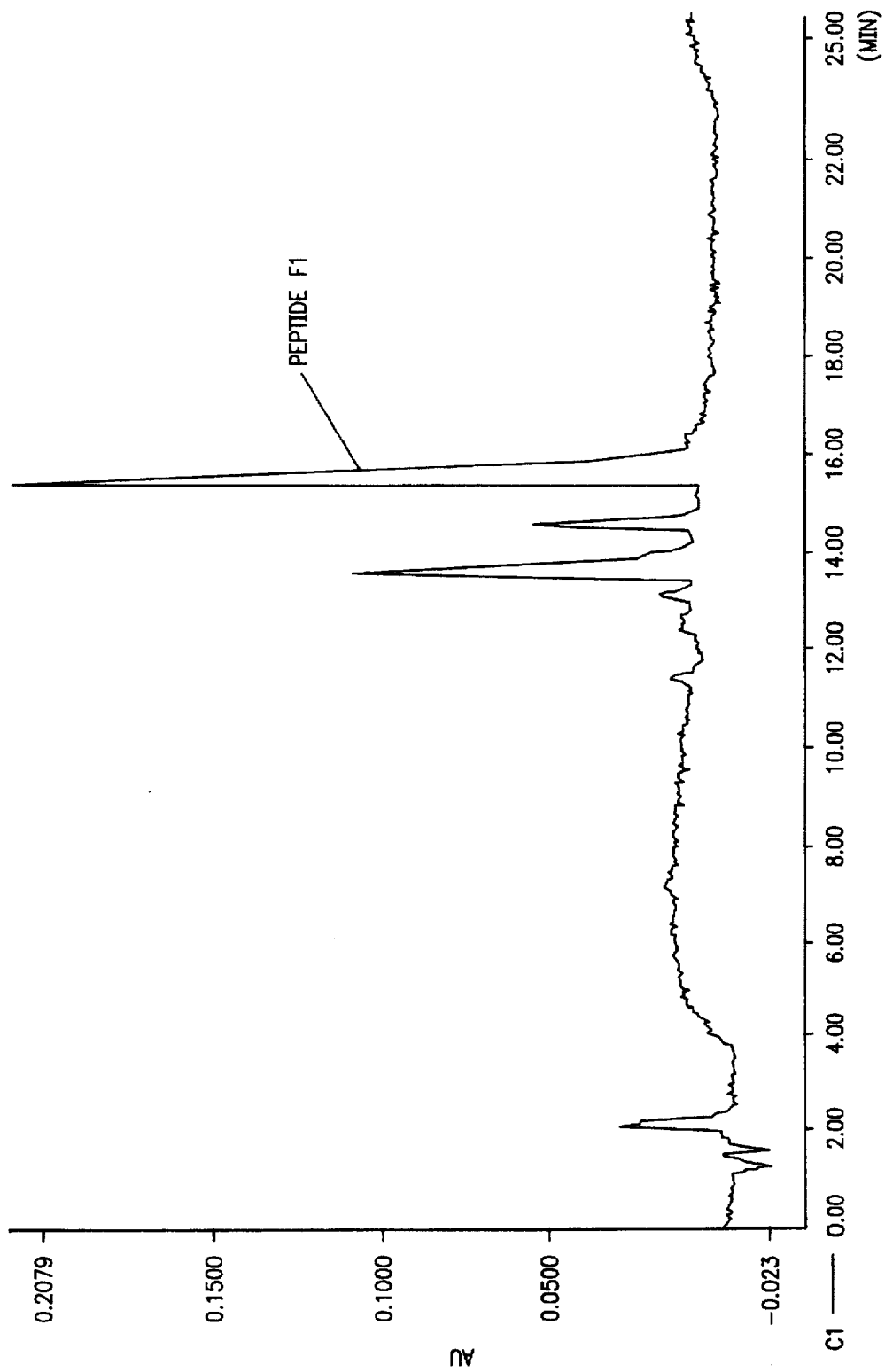

FIGS. 8 and 9 show the results for the preliminary fractionation of toxin F1. FIG. 8 shows the fractionation of the venom while FIG. 9 shows the secondary fractionation of crude F1.

Figure 10:
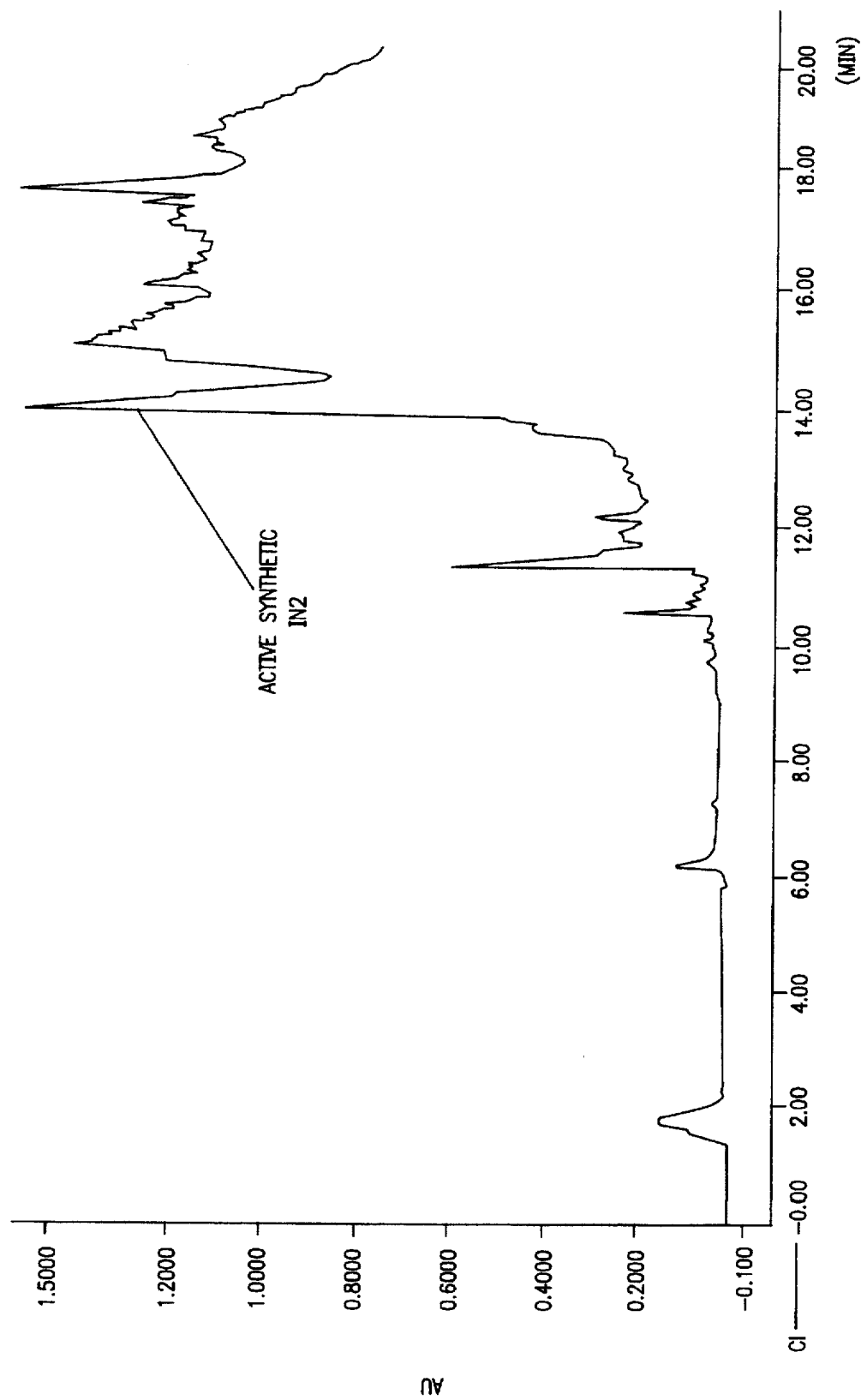

FIG. 10 shows results for RP-HPLC fractionation of refolding In2 (SEQ ID NO:2).

Figure 11:
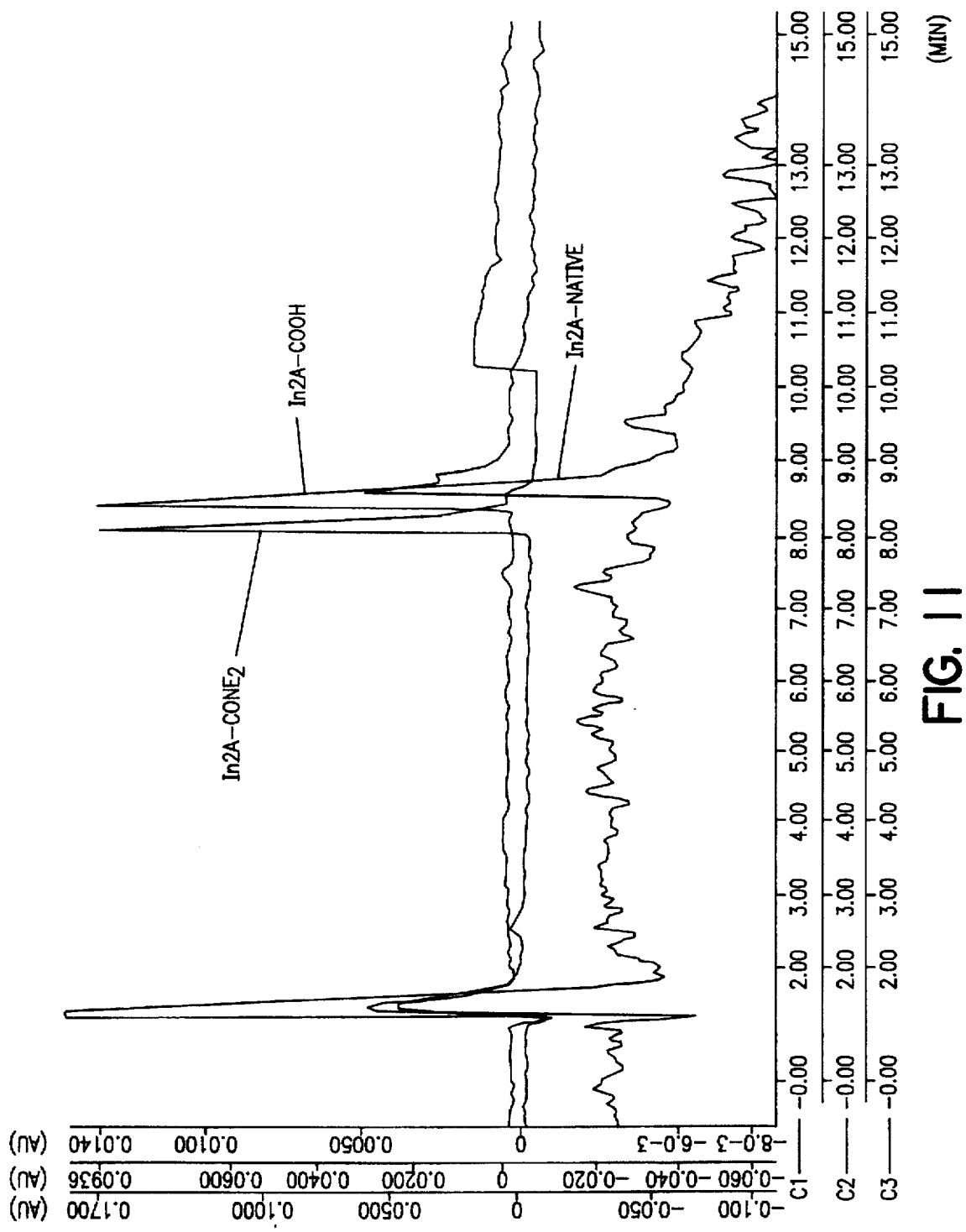

FIG. 11 shows RP-HPLC results for In2A-COOH (SEQ ID NO:9), In2A-CONH$_2$ (SEQ ID NO:10) and In2A-native.

Figure 12:
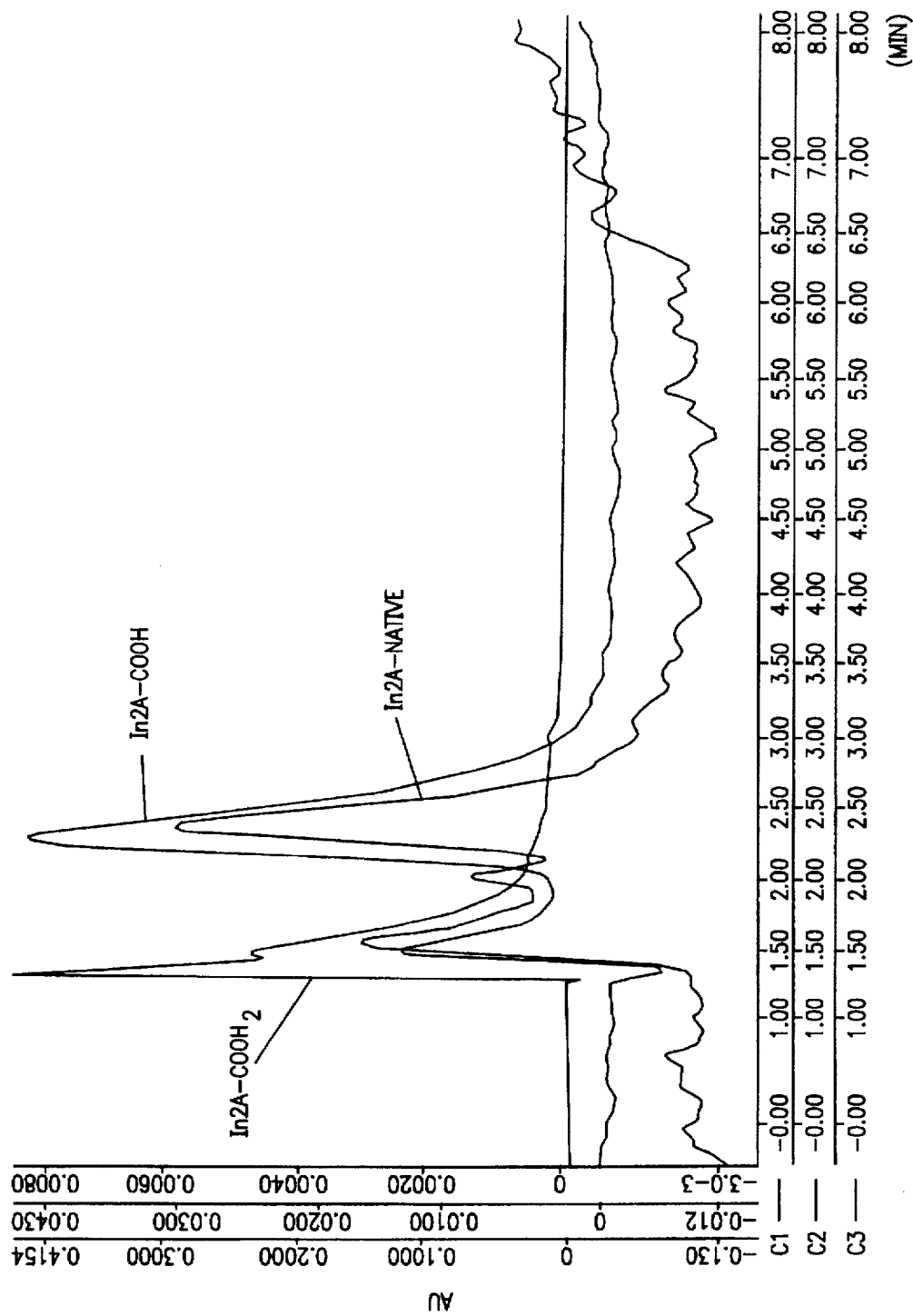

FIG. 12 shows cation exchange results for In2A-COOH (SEQ ID NO:9), In2-CONH$_2$ (SEQ ID NO:10) and In2A-native.

Figure 13:
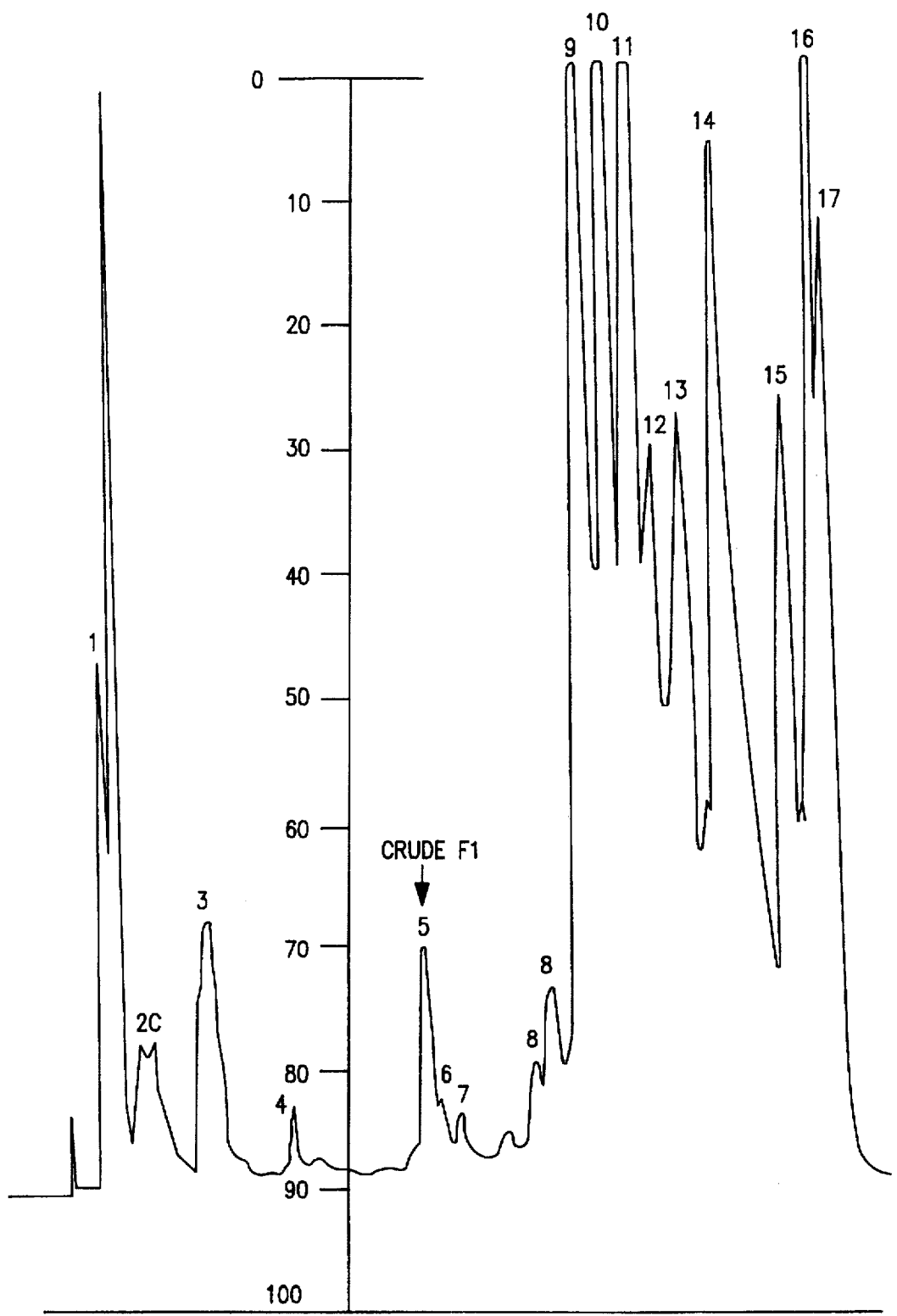
Figure 14:
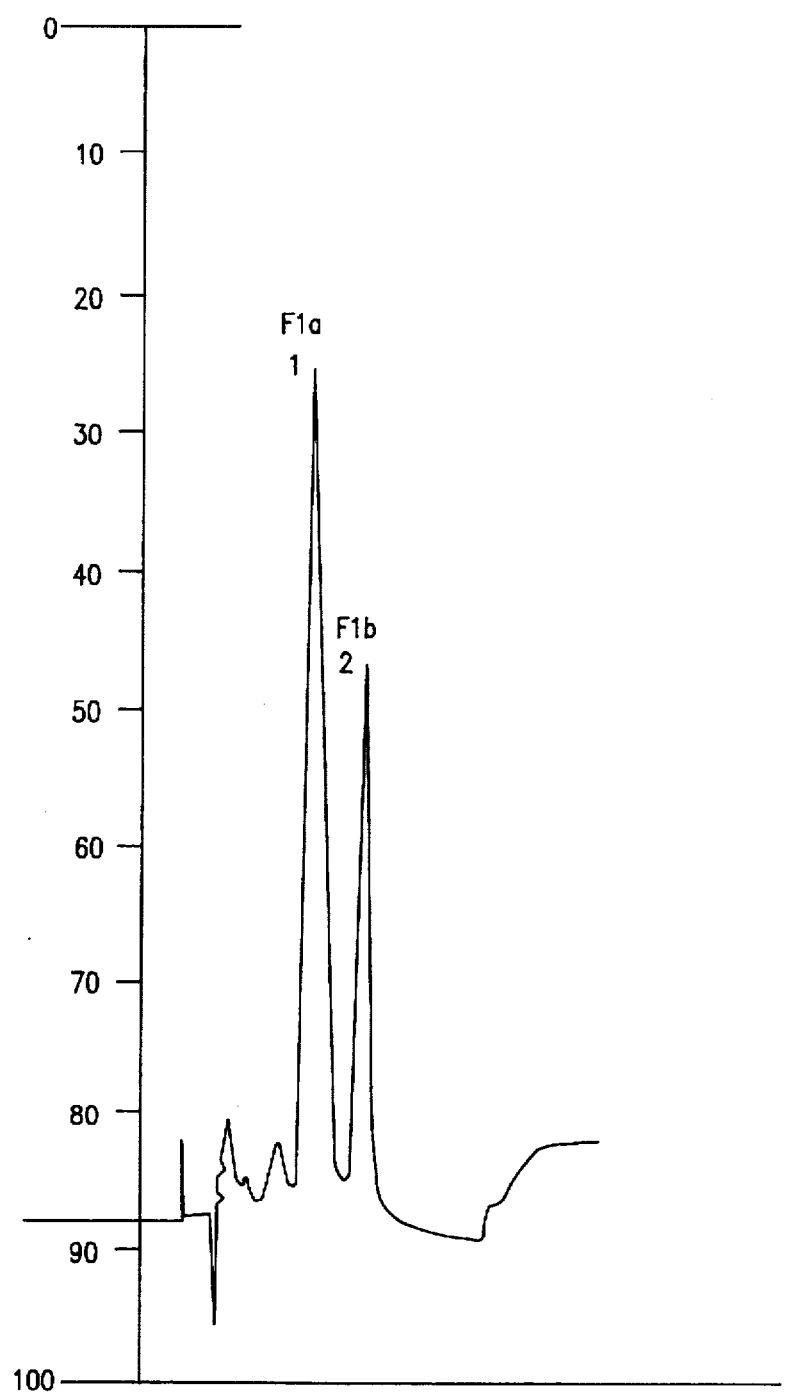

FIG. 13 shows a representative chromatographic profile of venom from *A. formidabilis*, with the following HPLC conditions:

Flow rate 1 ml/min
Buffer A 0.1% TFA/H$_2$O
Buffer B 0.1% TFA/80% acetonitrile
Detection UV abs @210 nm
Gradient
0_$^{24}$ 50% B
50_$^2$ 60% B
60_$^2$ 80% B
80_$^2$ 0% B FIG. 14 shows the secondary fractionation of crude F1 to reveal F1a and F1b under the following HPLC conditions:

Flow rate 1 ml/min
Buffer A 0.01M NH$_4$Ac pH 5.8
Buffer B 20% Buffer A, 80% acetonitrile
Detection UV abs @210 nm
Gradient 17% B to 24% B over 8 mins FIG. 15 shows the sequence results of gas phase sequencing for toxins F1a (SEQ ID NO:6 & SEQ ID NO:7) and F1b (SEQ ID NO:8).

FIG. 16 shows a CLUSTAL comparison of sequences between toxins of the invention.

FIG. 17 shows a CLUSTAL comparison of the funnel web toxins with published excitatory toxins.

FIG. 18 shows a CLUSTAL comparison of the funnel web toxins with published depressant toxins.

BEST MODE OF CARRYING OUT THE INVENTION

Materials

Spiders of the species *Atrax infensus* were collected within a few kilometers of Toowoomba, Queensland. The remaining spiders were collected in the Greater Sydney region.

All funnel-web species were milked by the relatively simple process of provoking them into the attack position then spontaneously collecting voided venom from the tips of the fangs.

Venom was collected by direct aspiration from live spider fangs into silanised (Coatasil, Ajax Chemicals, Australia) glass pipettes, and stored frozen at −20° C. until required. Venom was retrieved from the pipettes by repeated washing with 0.1% aqueous trifluoroacetic acid (TFA) and then freeze dried. Acetonitrile was purchased from Mallinckrodt Australia, trifluoracetic acid (TFA) and heptafluorobutyric acid (HFBA) from Pierce Chemical Co., dithiothreitol and 4-vinyl pyridine from Sigma Chemical Co., and endoproteinase Glu-C (*Staphylococcus aureus* V8 protease) from ICN Immunobiologicals, Costa Mesa, Calif., U.S.A. Iodoacetic acid was supplied by Merck Inc. All HPLC water used was produced by a Liquipure Modulab Water System, and vacuum filtered through a 0.45 μm Nylon membrane.

Culturing of Heliothis

The specimens of *H. armigera* used for the testing of spider venoms and venom fractions were kept in an air-conditioned laboratory and were raised by essentially the same methods as have previously been described for *H. punctigera* by Teakle, and Jensen[11]. Briefly, adult specimens (about 15 of each sex) of *H. armigera* were placed in 5 liter circular breeding chambers, the upper parts of which were lined with paper towels. Within 3–4 days the moths had mated and the females had laid their eggs on the paper towels. The eggs were washed off by gentle agitation of the paper towels in 0.2% sodium hypochlorite solution for 5 minutes. This also had the effect of surface-sterilizing the eggs.

The eggs were collected into damp tissue paper and then left in a 3 liter polyvinyl chloride bag until they hatched 1–2 days later. The resulting first-instar larvae were transferred into individual 30 ml plastic cups containing approximately 10 ml of a synthetic diet prepared from navy beans, wheat germ, Torula yeast, ascorbic acid, and sorbic acid, with Nipagin M and formaldehyde as preservatives. After approximately 12 days at 25° C., the larvae had reached the sixth-instar stage and were then either used for the testing of spider venoms/venom fractions or were allowed to pupate and eventually to emerge as new-generation adults.

Bioassay of Venoms and Fractions

Although crude funnel web venoms/venom fractions were found to be equally effective on both adult and sixth-instar larval Heliothis specimens, it was decided to perform essentially all testing on the last larval stage because the adults tended to die of natural causes a few days after emerging, whereas the larvae would demonstrate that the venom or fraction tested on them was toxic both by exhibiting abnormal movements and also by failing to pupate at the usual time.

It was recognised that final instar Heliothis larvae were likely to be relatively resistant to the actions of toxins but this was not considered a serious disadvantage because any venom or toxin effective against sixth-instar Heliothis larvae would probably be even more effective on any other insect.

Each venom or fraction was tested by gently restraining a larva and then injecting 5 μl of the venom/fraction under the lateral cuticle using a micro-syringe fitted with a 30 gauge needle. A total of ten larvae (six or seven for the later *A. formidabilis* venom fraction testings) were injected with venom/fraction and ten larvae (six or seven for the later *A. formidabilis* experiments) were also injected with 0.75% NaCl solution to serve as controls. The injected larvae were then returned to their individual culturing cups and observed for evidence of toxicity over the next three days. A crude venom or venom fraction was considered to have contained a toxic component if within three days most of the larvae had developed a pattern of constant and aimless writhing or had developed a pattern of constant and aimless writhing followed by death.

Venom Fractionation

Freeze dried venoms were reconstituted in 0.1% aqueous TFA to various concentrations of 10–50 mg/ml, and fractionated on a Pharmacia LKB HPLC system, utilising an LKB 2240 Rapid Spectral Detector in conjunction with LKB "Wavescan" data manipulation software. Columns used were a Waters Deltapak C18 (3.9 mm×150 mm, 10 μm×300 Å), and a Waters Deltapak C4 (7.8 mm×300 mm, 15 μm×300 Å) and a Biorad MA7P anion exchange (7.8 mm×50 mm). HPLC elution gradients were composed of an increasing acetonitrile concentration in a constant 0.1% TFA. Fractions were manually collected at chromatographic peaks into polypropylene containers and lyophilized.

Secondary fractionation was found to be necessary in the purification of the toxin MR1, in an increasing acetonitrile gradient and constant 0.05% HFBA. Again, fractions were manually collected and selected for sequencing on the basis of bioassay results.

For the the later experiments on *A. formidabilis* venom, freeze dried venom was reconstituted in 0.1% aqueous TFA to a concentration of 50 μg/μl, and fractionated by Reverse Phase HPLC on an ICI Kortec instrument using a Waters Deltapak column (3.9 mm×150 mm C18-300 Å), and UV detection at 210 nm. Elution gradients were composed of an increasing acetonitrile concentration in either 0.1% TFA, pH2 or 0.01M ammonium acetate, pH 5.8. Eluted components were detected by UV absorbance, and manually collected into polypropylene containers followed by lyophilisation.

Peptide Characterisation

Peptide sequencing was carried out on an Applied Biosystems Model 470A Gas Phase Sequencer using standard ABI programs with slight modification. PTH-amino acids were identified by an on-line Model 120A Analyser, also from Applied Biosystems.

Amino acid analysis was effected by use of a Waters Picotag Workstation, using either a Waters or Applied Biosystems HPLC system to quantitate PTC-amino acids. Samples were first hydrolysed in the gas phase using constant boiling hydrochloric acid in the gas phase containing 0.1% phenol at 150° C. for 1 hour.

A BioIon Biopolymer Mass Analyser (Applied Biosystems) was used for all mass spectral analysis work, typically at an accelerating voltage of 15000 Volts, and a collection time of about 2000 seconds (3,000,000 start pulses).

In the case of toxins F1a and F1b, alkylation and reduction was achieved using dithiothreitol in a standard TRIS reduction buffer at pH 8.2 followed by labelling of cysteine residues with 4-vinyl pyridine. The reduction mixture was then injected into the HPLC to isolate the pure reduced and alkylated peptide.

Enzymatic Digestion

Endoproteinase Glu-C (*Staphylococcus aureus* V8 protease) was used to cleave the reduced and alkylated peptides in an ammonium hydrogen carbonate buffer system at a pH of 7.8, essentially by the method of Houmard et al.[12], under conditions-designed to restrict the reaction to cleavage at glutamic acid residues only. Digests were fractionated by HPLC and resulting fractions were manually collected for further analysis.

Computer Alignment of Peptide Sequences

Peptide sequences were aligned and compared using the CLUSTALV[17] package, obtained from the author via the AARNET facility.

Initial Screening of Spider Species

A number of Heliothis trials were performed to demonstrate spider species with the potential to supply toxins with insecticidal value. The results are shown in Tables 6, 7, 8, and 9.

Isolation of Toxins

Figure 1:
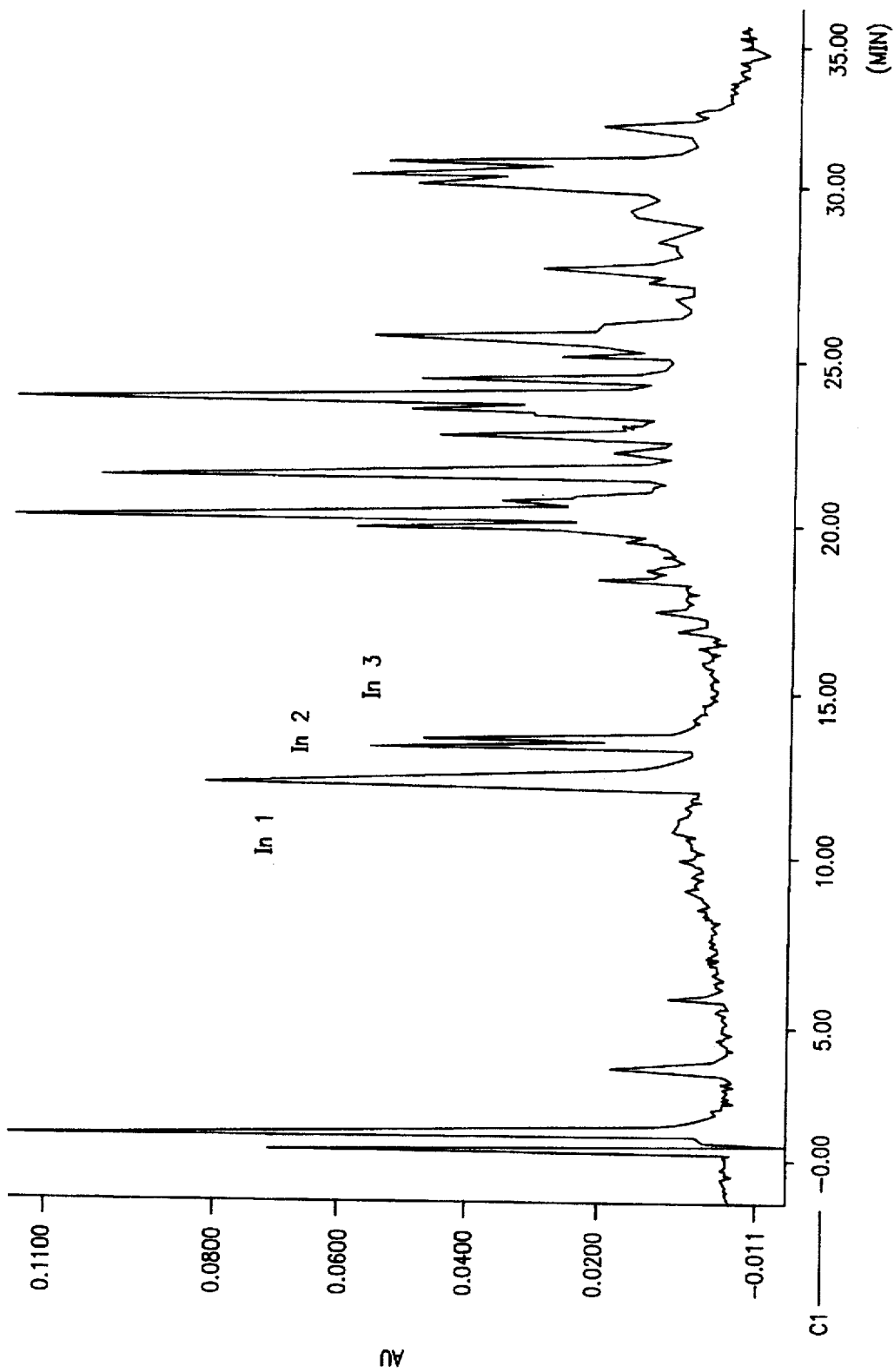
FIG. 1 shows the chromatographic profile of venom from female *Atrax infensus* spiders. The HPLC gradient was as follows: flow; 1 ml/min, 0–50% acetonitrile from 0–24 min, 50–60% from 24–29 min, 60–0% from 29–34 min.
Figure 2:
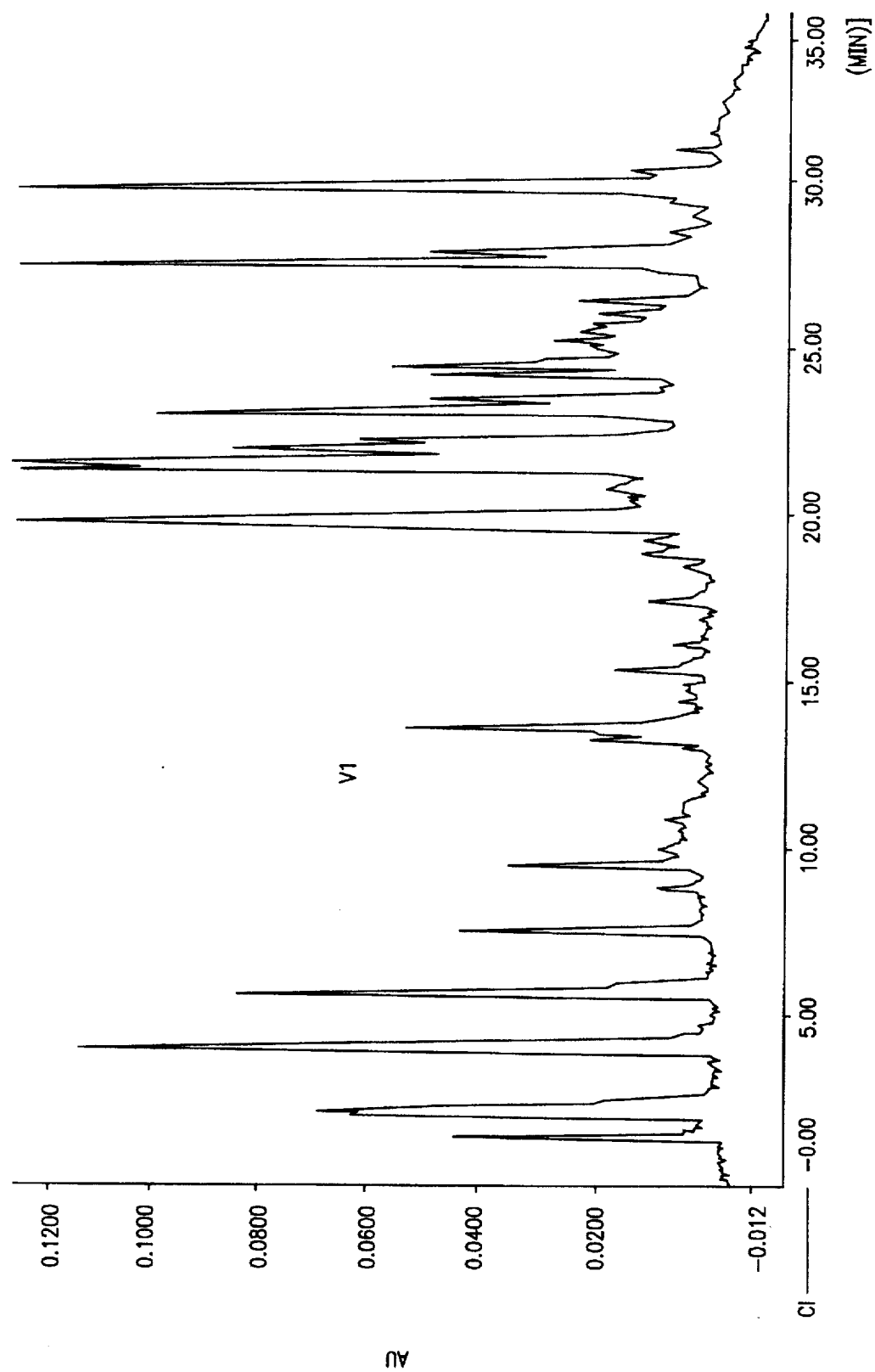
FIG. 2 shows the chromatographic profile of venom from female *Hadronyche versutus* spiders. The HPLC gradient was the same as for FIG. 1.
Figure 3:
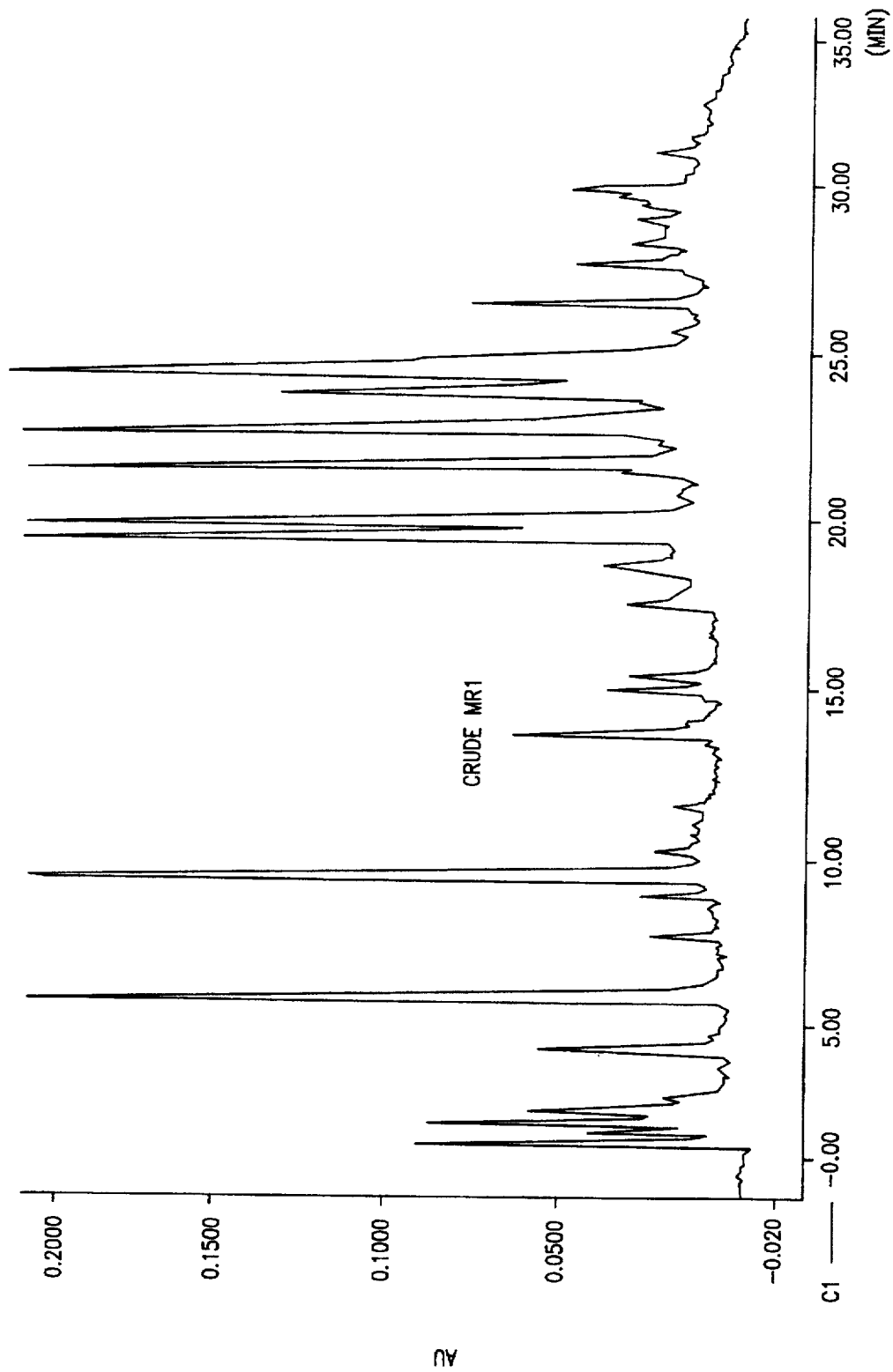
FIG. 3 shows the chromatographic profile of venom from male *Atrax robustus* spiders. The HPLC gradient was the same as for FIG. 1.
Figure 4:
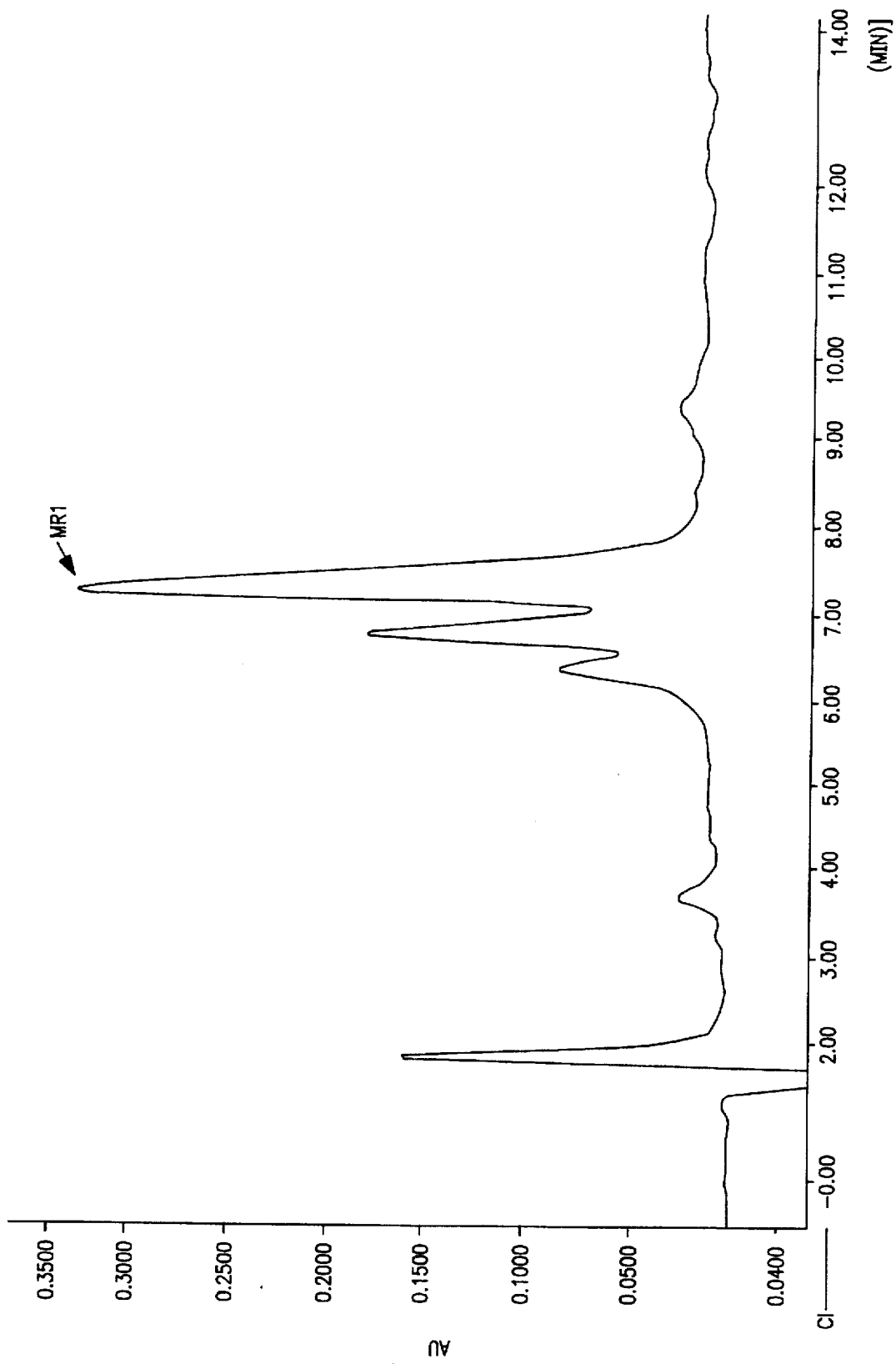
FIG. 4 shows the chromatographic profile for the refractionation of crude MR1 toxin. The HPLC gradient was as follows: flow; 1 ml/min, 20–35% acetonitrile from 0–15min, 35–50% from 15–20 min, 50–60% from 20–25 min, 60–20% from 25–28 min.

FIG. 1 shows the chromatographic profile of venom of female *Atrax infensus* spiders. Our bioassay procedure indicated that peaks marked In1, In2 and In3 possessed toxicity towards *H. armigera* larvae. Venoms from female *Hadronyche versutus* spiders (FIG. 2) and male *Atrax robustus* spiders (FIGS. 3 and 4) also showed active components named V1 (SEQ ID NO:5) and MR1 (SEQ ID NO:4) respectively when subjected to a similar fractionation/bioassay procedure. Bioassay results are presented in Table 1.

Female spiders of the species *Atrax infensus* were found to yield approximately 0.8 mg dry weight/milking. Female *H. versutus* spiders provided from 0.55 to 1.4 mg dry weight/milking. Venom from male *A. robustus* spiders was least abundant, milkings yielding only about 0.02 mg dry weight/milking. Toxin yields per mg dry weight of venom have been estimated and are presented in Table 1.

Five insect active toxins were isolated and characterised from Australian funnel web spider venoms, with sequences as shown in FIG. 5 (SEQ ID NO:1, SEQ ID NO:2, SEQ ID NO:3, SEQ ID NO:4 and SEQ ID NO:5). A feature of these toxins is the considerable homology of the series, in that twenty six of the thirty six (72%) or thirty seven (70%) amino acid residues are conserved throughout the series, particularly in the regions of the carboxyl termini.

Characterisation of Toxins

Gas phase sequencing of toxins In1 (SEQ ID NO:1), In2 (SEQ ID NO:2), In3 (SEQ ID NO:3), MR1 (SEQ ID NO:4) and (SEQ ID NO:5) gave the sequences shown in FIG. 5. Typically 500 pmol to 1 nmol of native toxin was loaded onto the sequencer support for each run. Cysteine residues were identified by subsequent sequencing of peptides reduced by dithiothreitol and alkylated by iodoacetic acid. To further clarify the carboxyl terminus regions In1, In2, In3 and V1 were digested with *S. aureus* V8 protease under conditions which restrict cleavage to the carboxyl side of glutamic acid residues. For In2 and In3 fractionation of these digests gave the chromatograms shown in FIG. 6. This gave carboxyl terminus peptides of nine or ten amino acids which were again subjected to gas phase sequencing, (residues underlined in FIG. 5) and were found to support the postulated sequences.

Amino acid analyses of the entire peptides, as well as *S. aureus* V8 fragments were also in agreement with the sequencing results, as shown in Table 2. Final confirmation of these structures was provided by Plasma Desorption Mass Spectrometry, in which ions correlating to the calculated masses were found in each case, see Table 3.

For V1, the resulting peptide digest was again fractionated by RP-HPLC, producing the chromatogram shown in FIG. 7. Collected fractions were subjected to amino acid analysis and gas phase sequencing as before and yielded the data shown in Table 4. As can be seen, the data derived from enzymatically produced fragments confirms the amino acid sequence derived from the intact peptide.

As has been stated previously, these toxins show considerable homology, particularly in the placement of the cysteine residues. From this we may infer that disulphide bridging will be the same in all the toxins. This is known to be of importance to the bioactivity since no detectable toxic effect was observed when reduced and alkylated In1 was put through the standard bioassay procedure. All cysteine residues appear to be involved in disulphide bridging, as no free cysteines were found in the native peptides by attempting alkylation without prior reduction, followed by gas phase sequencing.

Preliminary Analysis of *A. formidabilis* Venom

Venom from female *Atrax formidabilis* funnel web spider was examined.

The same HPLC fractionation columns, gradients and solvents were used as for toxin V1 (SEQ ID NO: 5), including secondary fractionation (FIGS. 8 and 9). As the amount of formidabilis venom available was severely limited no bioassay of the collected fractions was undertaken. Instead, the peak corresponding to V1 and R1 in *H. vertusus* and *A. robustus* fractionation chromatograms was selected for gas phase sequencing and amino acid analysis. The results of these analyses are shown in Tables 4 and 5.

While this data was not structurally definitive it indicated the presence of a sixth toxin in this venom.

Further Characterisation of *A. formidabilis* Toxin

Male and female spiders of the species *Atrax formidabilis* were milked of venom as described, yielding an average of 1.2 mg of venom (dry wt) per milking. Each milligram of venom yielded, on average, 8.8 and 4.2 µg of toxins F1a (SEQ ID NO:6 & SEQ ID NO:7) and F1b (SEQ ID NO:8) respectively after all processing, as quantified by UV absorption at 210 nm, based on the toxin V1 (SEQ ID NO: 5) ratio of 0.02 absorbance units/microgram dry weight.

Both toxins were found in venom from female spiders. Venom from specifically male spiders was not examined.

FIG. 13 shows a representative chromatographic profile of venom from *A. formidabilis* in constant 0.1% TFA. Similarity to venoms of other Australian Funnel-web species is apparent. The peak marked "Crude F1" corresponds to peaks with insecticidal activity in other related species. As this peak was suspected of being impure, a secondary fractionation in constant 0.01M NH$_4$Ac pH5.8 was undertaken, yielding the chromatographic profile depicted in FIG. 14, and clearly showing the presence of two components, now labelled F1a (SEQ ID NO:6 & SEQ ID NO:7) and F1b (SEQ ID NO:8). There is some question as to the carboxy terminal sequence for F1a. While all the other toxins have the C terminus, RCD, F1a appears to have CRND at the C terminus. However, the terminal D residue may be a sequencing artefact due to the breakdown of N to D in the sequencer. Mass spectral analysis of the molecule will reveal the correct C terminus. All fractions derived from this venom (equivalent to 2 mg dry wt.) were taken through the standard bioassay procedure, which indicated that only fractions F1a and F1b (A 1491-1 and A 1491-2, respectively) were active as shown in Table 10. Fraction A1477-6, while also showing some activity is almost certainly active only because of carry over from "Crude F1". Both fractions were subjected to Gas Phase Sequencing, the results of which describe the sequences shown in FIG. 15. Amino Acid Analysis was also carried out on F1a and F1b and the results are shown in Table 11.

Comparison of IN 1-3, V1 and MR1 with these two toxins reveals considerable homology in the case of F1b, and less, although still substantial, homology for F1a (see FIG. 16). The position of cysteine residues is remarkably consistent, being identical for six of the seven toxins; F1a being somewhat different in having two additional cysteine residues, and two others in slightly different positions. Conserved regions which may constitute an active site throughout the homologous series are not obvious, indicating that such a site may well be conformationally constructed, or else the bioactivity is conferred through some other mechanism.

FIG. 17 shows a comparison of the seven toxins with a group of excitatory, insect active spider and scorpion toxins retrieved from published literature. CLUSTAL has arranged the sequences, based on mathematical scoring of comparisons, with the amino terminal half of the Australian toxins aligned with the amino terminal region of the other toxins. It is obvious however, that only very limited similarity exists between the two groups. The Australian toxins are clearly distinct.

Likewise, a group of published insect active depressant toxins show negligible consensus with the Australian toxins in FIG. 18, which again indicates a clearly distinct group of toxins.

Sequence and Refolding of Toxin In2

The sequence of toxin In2 (SEQ ID NO: 2) was selected for synthesis in order to prepare biologically active peptide (i.e. peptide capable of interfering with normal neural activity). The production of biologically active and equivalent molecules by chemical synthesis is an important step in the application and commercialisation of any biotechnology. To overcome limitations in the supply of these natural toxins, we have synthesised and subsequently refolded toxin In2 (SEQ ID No: 2) to an active state.

Synthesis was performed on a Milligen 9050 peptide synthsizer using FMOC chemistry. FMOC pentafluorophenyl amino acid esters were added in 4-fold excess to an aspartic acid Pepsin KA resin (Milligen: 1.6 g; 0.09 mmol/g) in a stepwise manner starting from the C-terminus. Protecting groups were 4-methoxy-2,3,6-trimethylbenzenesulfonyl (for Arg), acetamidomethyl (Cys), t-butyl ester (Glu), t-butyloxycarbonyl (Lys), and t-butyl (Ser, Thr and Tyr). Double coupling of amino acids occurred at Thr-3, Ile-8, Thr-7, Gln-9, Cys-11 and Arg-35.

After the synthesis was completed, protecting groups were removed and the peptide chain was cleaved from the resin with trifluoroacetic acid/phenol (95:5 vol/vol) over a period of 6 hours. The resulting mixture was filtered and the filtrate evaporated to dryness. Anhydrous diethyl ether was added producing a white precipitate. This mixture was then filtered and the precipitate washed with ether and dried.

Removal of the Protecting Cys Groups (ACM)

The crude precipitate was dissolved in a minimum of 30% acetic acid. Twelve equivalents of mercury (II) acetate were added and the mixture stirred for 1 hour. 2-Mercapto-ethanol (200 µl) was added and stirred for 1 additional hour. The reaction mixture was filtered through Celite to remove the mercuric sulphide and washed with 30% acetic acid. The peptide was desalted by applying the filtrate to 4 C-18 Sep-Paks (Waters Associates) and washing with 0.19 TFA in water. The peptide was eluted with acetonitrile:water (1:1).

In2 Synthesis (Amide Resin)

The above procedure was followed except for the following:

0.6 g nova syn PR 500 resin (0.44 mmol/g) was used;
and Double coupling * -Asn-28, Glu-32, (Novabiochem) Gln-33, Asp-38 in addition to the double couplings that were performed in the synthesis above.

Refolding Protocol

Refolding of synthetic toxin In2, and formation of the correct disulphide bridging pattern was achieved using a Glutathione (Calbiochem) Redox buffer system. The buffer contained (per 20 mls, pH8.2):

242 mg Tris
5.8 mg EDTA
2 g guantidine hydrochloride
3.6 mg oxidised glutathione
18.4 mg reduced glutathione
2 mg synthetic peptide This reaction mixture was stirred overnight at room temperature and then fractionated by RP-HPLC using a Deltapak 3.9 mm×150 mm column and 0.1% TFA/acetonitrile gradient (FIG. 10). Fractions were collected and subjected to a similar bioassay procedure to the native peptides. Both amide and free acid carboxyl terminus forms of synthetic In2 were taken through this procedure.

Synthetic In2 with either free acid or amide C-terminus was successfully refolded and shown to be active at similar concentrations to the native toxin in the *H. armigera* bioassay. The fact that both forms were active indicates that the C-terminus may reside inside the molecule in the tightly coiled native form and consequently is less likely to be a region of the peptide that directly contributes to its toxicity.

Characterization of the Carboxyl Terminus

Insect active toxins and insect neuropeptides isolated previously[6,13] have had amidated carboxy-termini.

To clarify whether the C-terminus of these peptides exist as the free acid or in the amidated form, a comparative approach was adopted based on chemically synthesizing both the acid and amide forms of one of the peptides.

The endoproteinase Glu-C fragment of toxin In2 comprising the carboxyl terminal region was synthesized with either free acid terminus or amide terminus. Experimental peptide synthesis and deprotection were as described above.

Deprotected synthetic peptides were then alkylated using iodoacetic acid in a similar fashion to that used for native peptides. In this way, the exact equivalent to toxin In2 residues 29–37 was synthesized in either amide or acid form.

In2A-COOH NH$_2$-Asn-Gly-Asn-Gln-Val-Lys-Arg-Cys-Asp-COOH (SEQ ID NO:9)

In2A-CONH$_2$ NH$_2$-Asn-Gly-Asn-Gln-Val-Lys-Arg-Cys-Asp-CONH$_2$ (SEQ ID NO:10)

In2A-native NH$_2$-Asn-Gly-Asn-Gln-Val-Lys-Arg-Cys-Asp-?

The HPLC elution characteristics of these three peptides were then compared using both a Reverse Phase HPLC column (FIG. 11) (Waters Deltapak 3.9 mm×150 mm×5 µm) and a cation exchange column (Polycat A, 4.6 mm×250 mm×5 µm, PolyLC, Activon, Melbourne, Australia) (FIG. 12).

FIG. 11 shows In2A-native coeluting with synthetic In2A-COOH indicating that the native peptide exists as the free acid. To further confirm this cation exchange HPLC also shows (in FIG. 12) In2A-native co-eluting with In2A-COOH.

The carboxyl terminus of In2 was consequently shown to be in its free acid form. By inference, other members of the homologous series are also likely to have free acid carboxyl termini.

Effective Dose for V1 Toxin

Sixth-instar Heliothis larvae (10 per dose) were injected with V1 toxin in a 5 µl volume. The number dead or writhing after 24 hours was recorded. The percentage dead or writhing was plotted rather than percentage dead as the percentage dead in 24 hours was too variable. Thus the ED$_{50}$ not the LD$_{50}$ is provided.

| Dose (µg) | % Dead or Writhing | % Dead |
|---|---|---|
| 0 | 0 | 0 |
| 1 | 0 | 0 |
| 2 | 20 | 0 |
| 3 | 20 | 10 |
| 4 | 20 | 10 |
| 6 | 40 | 0 |
| 7.5 | 70 | 0 |
| 10 | 100 | 0 |
| 15 | 70 | 10 |
| 20 | 90 | 10 |
| 40 | 100 | 60 |
| 60 | 90 | 10 |

Probit estimation of the effective dose (50%) for V1 toxin on Heliothis was based on the method of Finney D. J. (1971)[14]. The results are plotted in FIG. 7. The ED$_{50}$ was determined to be 7 µg/larva.

Twenty Heliothis larvae (sixth instars) were weighed. The mean weight was 502.4 mg and the range was 389–607 mg. Thus the ED$_{50}$ estimation can also be stated as 14 µg/g.

The weight of the adult blowfly (*Lucilia cuprina*) was estimated as approximately 0.06 g, the Heliothis larva therefore being 8 times heavier.

Since 10 micrograms of V1 toxin was effective on adult blowflies in 4 hours (see above) and 7 µg produced writhing in the Heliothis larvae in 24 hours, it would appear that the potency of this toxin on the two insect species is comparable.

Work with both crude funnel web venoms and purified toxins has shown that these toxins can cause uncontrolled movements in less than 24 hours, and as little as 7 hours was needed on some occasions. Since similar effects were produced in adult blowflies in 10 minutes when a high toxin dose was used, there is reason to expect that the speed of action of these toxins in Heliothis larvae could also be greatly increased if the dosage was increased. While it seems unlikely that the speed of action of these toxins could achieve the speed of action of existing toxins such as the pyrethroids, an insecticide which stops its target insects from feeding within a few hours should find commercial acceptance.

Toxicity of Toxin V1 to Newborn Mice

In order to establish the relative toxicity of toxin V1 (compared to the mammalian *H. versutus* toxin Vesutoxin) a bioassay involving newborn mice was undertaken. A total of eight newborn (less than 24 hours old) Swiss Outbred mice were weighed to establish an average weight per mouse of 1.75 g. The mice were divided into a Control group of four mice, and a Test group of the other four mice. The bioassay procedure followed was based on that of Sheumack et al. (1984)[15] and Sutherland (1980)[16]. Mice in the Test group each received a single dose of 4.4 µg of Toxin V1 in 20 µl of 1% acetic acid, injected subcutaneously into the dorsum using a microliter syringe (Scientific Glass Engineering). Mice in the control group each received a similar injection of 20 µl of 1% acetic acid only. Mice were then observed hourly for the first 6 hours, then at 24 hours.

All mice in both groups survived apparently unaffected beyond 24 hours post injection. The toxin dose administered 2.5 mg/kg of mouse had been calculated to be five times, by mass, the LD$_{50}$ dose of Vesutoxin, as determined by Sheumack et al. (1984)[15] under similar experimental conditions. This result serves to highlight the relative inactivity in mammals of the insect active toxin V1 when compared to the mammalian toxin Vesutoxin.

Tests of Purified and Synthesized Funnel Web Toxins

Initial attempts to sequence the active fraction from the reversed-phase HPLC fractionation of male *A. robustus* venom indicated it was impure. Hence a 3 mg sample was subjected to further purification and three potentially active fractions were then tested, the results being as follows:

Fraction R1a: Of 8 Heliothis larvae, all survived for 24 hours but 7 were dead after 48 hours with no convincing evidence of aimless writhing.

Fraction R1b: Of 7 larvae, all survived for 24 hours but were dead after 48 hours, again with no clear evidence of writhing. Fraction R1c: Of 7 larvae, 6 had apparent writhing in 24 hours and all 7 were dead in 48 hours.

Because of the comparatively large amount of female *A. infensus* venom available, the active fraction from this venom was the first to be subjected to amino acid sequencing and subsequent synthesis. An initial preparation of synthesized material believed to be equivalent to 50 µg micrograms of toxin was prepared and tested on Heliothis larvae in the usual manner. Three fractions were obtained from this synthesis and the resulting assay results were as follows:

Peak F (eluting as for native In2): Within 72 hours three of the five larvae injected showed the characteristic aimless writhing caused by the native toxin.

Peak G (a possibly impure fraction eluting immediately after Peak F): None of the five larvae injected showed adverse effects in 72 hours.

Peak H (considered to be the reduced synthetic starting material): None of the five injected larvae showed adverse effects in 72 hours.

Saline Controls: Five larvae were injected with 5 μl of insect saline and suffered no apparent ill-effects over the next 72 hours.

Since the amount of material available for assay in this first synthesis trial was so small, the experiment was repeated with a slightly increased quantity of starting material. The assays of the fractions apparently equivalent to Peaks F, G and H were:

Fraction 5: Six of 7 injected larvae developed aimless writhing within 24 hours.

Fraction 6: All 7 larvae remained in good health after 24 hours.

Fraction 7: Six of the 7 larvae survived 24 hours, the seventh dying without exhibiting writhing.

Saline Controls: All 7 larvae remained in good health for at least 24 hours.

In a third In2 refolding experiment, starting material equivalent to approximately 1.7 mg of crude *A. infensus* venom was converted either to the acid form (B695-7) or to the amide form (B694-7). The assay data then recorded was:

Acid Form: All six larvae used were unaffected by this preparation over 72 hours.

Amide Form: All 10 larvae used developed aimless writhing in 24 hours.

Saline Controls: All 8 larvae remained in good health after 72 hours.

Because it was expected that the acid form of In2 would be insecticidal if correctly refolded, another attempt at producing it was made, the assay results this time being:

B746-1 (equivalent to about 3 mg original venom): Aimless writhing was observed within 24 hours and 7 of 9 larvae were either still writhing or had died within 3 days.

B746-2 (also equivalent to about 3 mg of venom): All 9 injected larvae were dead or writhing within 3 days.

Saline Controls: All 9 injected larvae survived 3 days with no ill effects.

Assays on Other Species

Injections of female *A. infensus* venom were made into five insect species of domestic or economic importance. Testing was performed on the coleopteran mealworm beetle *Tenebrio molitor*, the cockroach *Periolaneta americana*, the Australian plague locust *Chortoicetes terminifera*, the hemipteran *Musgraveia sulciventris* and a blowfly species thought to be an Amenia species (this field isolate has not been fully classified).

The cockroach species was obtained from the University College of Southern Queensland, Toowoomba, Queensland, Australia as a laboratory culture. The other species were obtained by collection in the field when needed.

Coleopteran Mealworm Beetle—*Tenebrio molitor*

Three μl of venom were injected into the latero-ventral abdomens of 5 adult beetles which had been anaesthetized lightly with carbon dioxide gas. No initial excitement was seen but within 10 minutes all beetles were inert and appeared dead. No recoveries were noted over the next 24 hours.

Of 6 beetles that were injected with insect saline instead of venom, all survived at least an hour, three for more than 6 hours and two for 24 hours. This showed that Tenebrio is a delicate test insect but that the injected spider venom was toxic to it.

Cockroach—*Periplaneta americana*

Four μl of venom were injected into the latero-ventral abdomens of 5 adult (or late nymph) specimens. Within 30 minutes all but one was completely inert although all had recovered 6 hours later. Curiously, 3 of these cockroaches were found to have died 24 hours later.

None of 4 saline-injected cockroaches was affected in any way over the same 24 hour period.

Australian Plaque Locust—*Chortoicetes terminifera*

This smaller field grasshopper species was collected locally and 4 μl of venom was injected into the antero-lateral abdomens of 5 anaesthetized specimens (adults or late nymphs). All were paralysed within 10 minutes and did not recover over the next 24 hours.

Another 5 specimens were injected with insect saline and suffered no ill-effects over the next 24 hours.

Bronze Orange Bug—*Musgraveia sulciventris*

Four μl of venom were injected into the latero-ventral abdomens of 5 anaesthetized mid-nymphal specimens. All were inert and apparently dead 10 minutes later, no recoveries occurring during the next 24 hours.

No ill-effects were noted in 4 other specimens that were injected with insect saline instead of venom.

Dipteran Blowfly

Only adults of this insect were readily available. These were so drastically affected by *A. infensus* venom that a microsyringe contaminated with this venom and then filled with 1.0 μl of insect saline was almost immediately paralytic when the injection was performed on 9 specimens. Some recoveries were observed 6 hours later but it was obvious that blowflies were very sensitive to this venom.

Of 5 specimens injected with insect saline as controls, none was initially affected and all survived at least 6 hours. Unfortunately, the injection trauma made the interpretation of this trial more difficult than it otherwise would have been.

In summary, these initial tests of *A. infensus* venom on the 5 insect species used indicated that this venom is insecticidal to many more insect species than just *H. armigera*.

Effect of Purified V1 Toxin on Insects Other Than Heliothis

To determine the activity of this toxin group on insects other than *H. armigera*, a total of 10 mg of crude venom was fractionated as described above and divided into 5 sample lots. The five sample lots were then used in bioassays against other insects.

Coleopteran Mealworm Beetle—*Tenebrio molitor*

Final stage larvae of the mealworm *Tenebrio molitor* were tested with purified V1 toxin. Sets of 8 larvae were each injected with 3 μl of insect saline containing 0.2, 0.02, 0.002 or 0 mg of V1 toxin. All appeared unaffected for the first 24 hours, but at 48 hours all 8 of the highest dose larvae and 6 of the second highest dose larvae were showing the characteristic writhing this toxin causes. The low dose and control larvae were all unaffected over 48 hours.

Blowfly—*Lucilia cuprina*

Adults of the blowfly *Lucilia cuprina* were obtained from the University of Queensland's Entomology Department. Sets of 8 adults were each injected (dorsal thorax) with 1.0 μl of V1 toxin in insect saline, producing doses of 100, 10, 1, 0.1 and 0 μg of toxin per insect. All 8 that received the highest dose showed uncontrolled movements within 10 minutes and were dead in 4 hours. The 10 μg dose caused one death in 4 hours and the remaining 7 were dead at 24 hours. The two lower doses and the controls all survived without apparent effect for 24 hours.

Bronze Orange Bug—*Musgraveia sulciventris*

V1 toxin was also tested against the bronze orange bug *Musgraveia sulciventris*. Supplies of this insect were limited but 8 adult specimens were given by injection 5 μl of V1 toxin in insect saline, this being equivalent to 0.2 mg of the purified toxin. Three showed uncontrolled movements in 24 hours and all 8 were dead in 48 hours. Six late instar nymphs were given 3 μl (since they were smaller than the adults) of the toxin (a 1/10 dose equivalent to 0.012 mg V1) but all survived 2 days, as did 8 control adults injected with 5 μl of insect saline.

15

Cockroach—*Periolaneta americana*

A group of eight cockroaches were injected, this time with purified V1 toxin (a 5 µl injection equivalent to 0.2 mg of venom). Toxic effects were apparent in 6 of the 8 specimens within 6 hours, two being severely envenomated. The most obvious effect was uncontrolled movements of the legs and mouthparts. Over the next 3 days these cockroaches however gradually recovered fully.

Again, 8 control cockroaches were totally unaffected by their saline injections.

Australian Plague Locust—*Chortoicetes terminifera*

A group of 8 grasshoppers were injected with purified V1 toxin at a dosage equivalent to 0.2 mg per specimen. All 8 were dead or exhibiting spontaneous twitching within 6 hours and failed to recover over the next 18 hours.

A second group of 8 grasshoppers was then injected with the same toxin at a 0.02 mg dosage. Of these, 3 were dead and another 4 exhibited spontaneous twitching in 24 hours, 7 having died by the 36th hour.

A total of 9 grasshoppers were injected with insect saline as controls. All of these survived at least 24 hours with no ill-effects.

In summary, these bioassay injection trials show that these toxins are effective, and may be of use in control of insects other than the cotton bollworm, Heliothis.

Venom Feeding Trials

A total of 100 µl of pooled female *A. infensus* venom was mixed with 1.0 ml of normal *H. armigera* diet as this was being poured. Once set, this envenomated diet was then divided into 10 equal portions, these being placed in ten 10 ml plastic tubes and a third instar *H. armigera* larva added to each tube. It was found after 24 hours that all larvae had entirely consumed their portion of the diet so they were then returned to the normal diet. None of the larvae were adversely affected and all pupated normally at the usual time.

TABLE 1

TOXIN YIELDS AND BIOASSAY RESULTS

| Toxin | Yield/mg[a] dry venom (pmol) | Larvae affected[b] 24 hr | 48 hr | 72 hr | Estimated[c] dose/larva pmol (µg) |
|---|---|---|---|---|---|
| *Atrax infensus* (female) | In1  1256 | 4/8 | 7/8 | 7/8 | 942 (4) |
|  | In2  1056 | 7/8 | 8/8 | 8/8 | 792 (3) |
|  | In3  700 | 3/8 | 6/8 | 6/8 | 525 (2) |
| *Hadronyche versutus* (female) | V1  1228 | 4/8 | 7/8 | 7/8 | 767 (3) |
| *Atrax robustus* (male) | MR1  165 | 3/7 | 6/7 | 6/7 | 94 (0.3) |

[a] Yields and doses were estimated indirectly from amino acid analysis and gas phase sequencing (no allowance was made for losses during isolation).
[b] As defined in "Bioassay of Venoms and Fractions" section. The left hand number in each pair is the number affected. The right hand number is the total number tested.
[c] Dose actually injected. The weight (mg) is given in brackets. These are equivalent to the specified molar quantities.

TABLE 2

AMINO ACID ANALYSIS DATA

Complete Peptides

|  | In1 |  | In2 |  | In3 |  | MR1 |  | V1 |  |
|---|---|---|---|---|---|---|---|---|---|---|
|  | Cal. | Seq. | Cal. | Seq. | Cal. | Seq. | Cal. | Seq. | Cal. | Seq. |
| Asx | 4.9 | 5 | 5.7 | 6 | 5.3 | 6 | 5.3 | 5 | 5.7 | 6 |
| Glx | 4.1 | 4 | 5.1 | 5 | 3.9 | 4 | 5.4 | 5 | 5.2 | 5 |
| Ser | 3.4 | 4 | 2.8 | 3 | 4.1 | 4 | 4.6 | 5 | 4.0 | 4 |
| Thr | 3.6 | 4 | 2.7 | 3 | 2.7 | 3 | 2.3 | 2 | 2.8 | 3 |
| Gly | 2.2 | 2 | 2.4 | 2 | 2.3 | 2 | 3.0 | 3 | 3.0 | 2 |
| His | 0.9 | 1 | — | 0 | — | 0 | 1.1 | 1 | — | 0 |
| Ala | 1.2 | 1 | 1.1 | 1 | 1.2 | 1 | — | 0 | — | 0 |
| Tyr | 2.0 | 2 | 2.0 | 2 | 1.8 | 2 | 1.7 | 2 | 0.8 | 1 |
| Arg | 1.3 | 1 | 1.3 | 1 | 2.2 | 2 | 1.4 | 1 | 1.6 | 1 |
| Pro | 3.2 | 3 | 3.9 | 4 | 2.4 | 2 | 2.6 | 3 | 3.8 | 4 |
| Val | 1.1 | 1 | 1.1 | 1 | 1.1 | 1 | 1.8 | 2 | 1.0 | 1 |
| Phe | — | 0 | — | 0 | — | 0 | — | 0 | 1.0 | 1 |
| Ile | — | 0 | 0.9 | 1 | 0.8 | 1 | 0.9 | 1 | 1.0 | 1 |
| Lys | 2.0 | 2 | 2.0 | 2 | 2.2 | 2 | 1.0 | 1 | 2.2 | 2 |
| Cys | —[a] | 6 | —[a] | 6 | —[a] | 6 | —[a] | 6 | —[a] | 6 |

*S. aureus* V8 digest, Carboxyl Terminus Fragments

|  | In1 |  | In2 |  | In3 |  |
|---|---|---|---|---|---|---|
|  | Cal. | Seq. | Cal. | Seq. | Cal. | Seq. |
| Asx | 3.2 | 3 | 2.4 | 3 | 3.1 | 3 |
| Glx | 1.1 | 1 | 1.3 | 1 | 1.1 | 1 |
| Gly | 1.0 | 1 | 1.5 | 1 | 1.1 | 1 |
| Arg | 0.9 | 1 | 1.0 | 1 | 0.9 | 1 |
| Val | 0.85 | 1 | 0.9 | 1 | 0.9 | 1 |
| Lys | 0.9 | 1 | 0.9 | 1 | 0.9 | 1 |

[a] Not Determined.
Cal Ratio calculated from amino acid analysis.
Seq Ratio determined from amino acid sequence.

TABLE 3

PLASMA DESORPTION MASS SPECTROMETRY RESULTS

| Toxin | Mass Calculated from Sequence | Mass Measured |
|---|---|---|
| In1 | 3929 | 3929 |
| In2 | 4055 | 4057 |
| In3 | 4058 | 4049 |
| V1 | 4050 | 4048 |
| MR1 | 4005 | 4005 |
| In1 V8 fragment 28–36 | 1092 | 1094 |
| In2 V8 fragment 29–37 | 1092 | 1094 |
| In3 V8 fragment 29–37 | 1092 | Insufficient signal |

TABLE 4

AMINO ACID ANALYSIS AND GAS PHASE SEQUENCING DATA FROM ENDOPROTEINASE Glu-C DIGESTED FRAGMENTS OF TOXIN V1

Amino Acid Analysis

| | Fragment A | | Fragment B | | Fragment C | |
|---|---|---|---|---|---|---|
| | Calc. | Exp. | Calc. | Exp. | Calc. | Exp. |
| Asx | 2.38 | 3 | 2.05 | 2 | 1.18 | 1 |
| Glx | — | 0 | 2.75 | 2 | 2.12 | 2 |
| Ser | — | 0 | 2.20 | 2 | 1.99 | 2 |
| Gly | 2.27 | 1 | — | 0 | 1.18 | 1 |
| Thr | 0.89 | 1 | 0.99 | 1 | 0.95 | 1 |
| Pro | — | 0 | — | — | 3.76 | 4 |
| Tyr | — | 0 | — | — | 0.91 | 1 |
| Cys | N.D. | 1 | 2.20 | 3 | 2.07 | 2 |
| Ile | — | 0 | — | — | 0.83 | 1 |
| Phe | — | 0 | 0.92 | 1 | — | — |
| Lys | 0.79 | 1 | 0.99 | 1 | — | — |
| Val | 0.99 | 1 | — | — | — | — |
| Arg | 0.69 | 1 | — | — | — | — |

Gas Phase Sequencing

Fragment A
NH$_2$—Asn—Gly—Asn—Thr—Val—Lys—Arg—CMCys—Asp—COOH
(SEQ ID NO:11)

Fragment C
NH$_2$—Ser—Pro—Thr—CMCys—Ile—Pro—Ser—Gly—Gln—Pro—CMCys—Pro—Tyr—Asn—Glu—COOH (SEQ ID NO:12)

Calc. Calculated Ratio.
Exp. Experimental Ratio.
N.D. Not Determined.

TABLE 5

Atrax formidabilis TOXIN PRELIMINARY STRUCTURAL DATA

Amino Acid Seguence[1]

NH$_2$—Ser—Pro—Thr—?—Thr—Gly—Ala—Asp—Arg—Pro—?—Ala—Ala—?—?—Pro—?—?—Pro—Gly—Thr—Ser—?—Lys—Gly—Pro—Glu—Pro—Asn—Gly—Val—Ser—Tyr—?—Arg—Asn—Asp—COOH.

TABLE 5-continued

Atrax formidabilis TOXIN PRELIMINARY STRUCTURAL DATA

Amino Acid Analysis

| Amino Acid | Calculated Ratios | | Experimental Ratio[2] |
|---|---|---|---|
| | Dupl. 1 | Dupl. 2 | |
| Asx | 4.04 | 3.90 | 4 |
| Glx | 1.15 | 1.37 | 2 |
| Ser | 3.46 | 3.57 | 3 |
| Gly | 4.30 | 4.41 | 4 |
| Arg | 2.74 | 3.05 | 2 |
| Pro | 6.06 | 5.57 | 6 |
| Tyr | 1.01 | 0.95 | 1 |
| Lys | 0.87 | 0.84 | 1 |
| Val | 1.01 | 0.95 | 1 |

[1]Gaps in the amino acid sequence represent sequencer cycles where no amino acid could be assigned, these amino acids may be cysteine residues.
[2]Experimental Ratio determined from amino acid sequence.

TABLE 6

EFFECTS OF FEMALE WHOLE VENOM (A. infensus) (4 μl per larva)

| SPECIES | NO. OF LARVAE USED | EFFECTS OBSERVED |
|---|---|---|
| A. infensus | 10 | All larvae developed a pattern of aimless writhing within 24 hours and failed to pupate, mostly dying in 5 days |
| 0.75% NaCl | 10 | All larvae were unaffected and pupated at the normal time |

TABLE 7

EFFECTS OF OTHER FUNNEL WEB VENOMS (4 μl per larva)

| SPECIES | NO. OF LARVAE USED | EFFECTS OBSERVED |
|---|---|---|
| A. robustus (male) | 10 | 1 larva showed writhing in 24 hours but 4 were dead in 5 days |
| H. formidabilis (female) | 10 | 7 larvae were writhing in 24 hours |
| H. versuta (female) | 10 | 9 larvae were writhing in 24 hours |
| 0.75% NaCl | 10 | All larvae were unaffected and pupated at the normal time |

TABLE 8

A. robustus VENOM FRACTION TESTS ON H. armigera

| Sex of spider | HPLC system used | Total no. of fractions tested | Fraction(s) exhibiting definite toxicity |
|---|---|---|---|
| male | reversed phase | 8 | Fraction 2; writhing produced in 9 of 10 larvae; 18 moths with uncontrolled movements in 15 mins and dead in 24 hours |
| female | reversed phase | 11 | Fractions 9–11 caused death or writhing in 24 hours on sets of 7 larvae |

TABLE 8-continued

A. robustus VENOM FRACTION TESTS ON H. armigera

| Sex of spider | HPLC system used | Total no. of fractions tested | Fraction(s) exhibiting definite toxicity |
|---|---|---|---|
| female | ion exchange | 8 | Deaths of almost all larvae (sets of 7) in all fractions |
| female | reversed phase | B385 (6–8) | Fraction 7 caused writhing in 4 of 5 larvae in 24 hours |
| female | reversed phase | B392 (7–9) | Fraction 9 caused writhing in 2 of 5 larvae in 24 hours |

TABLE 9

FEMALE H. versuta AND A. infensus
VENOM FRACTION TESTS ON H. armigera

| Weight of venom used (mg) | No. of fractions tested | Code No. | Fractions exhibiting definite toxicity |
|---|---|---|---|
| 4 (vers) | 22 | A51 | Fraction 10 (sets of 8 larvae) |
| 2 (vers) | 21 | B97 | Fraction 8 (sets of 10 larvae) |
| 6 (vers) | 16 | B84 | Fraction 9 (sets of 10 larvae) |
| 10 (vers) | 3 | B121 | Fractions 7–9 (7 most potent and 8 least potent; sets of 8 larvae) |
| 2 (vers) | 4 | A140 | Fractions 3, 4 (3 the worst; sets of 8 larvae) |
| 6 (inf) | 16 | B111 | Fractions 7–9 (all potent on sets of 8 larvae) |

(vers) H. versuta
(inf) A. infensus

TABLE 10

A. formidabilis BIOASSAY RESULTS

| Fraction | No of Larvae Injected | NUMBER SHOWING WRITHING AFTER | | |
|---|---|---|---|---|
| | | 24 hours | 48 hours | 72 hours |
| A 1477-1 | 7 | 0 | 0 | 0 |
| A 1477-2 | 7 | 0 | 0 | 0 |
| A 1477-3 | 7 | 0 | 0 | 0 |
| A 1477-4 | 6 | 0 | 0 | 0 |
| A 1491-1 (F1a) | 7 | 4 | 5 | 5 |
| A 1491-2 (F1b) | 7 | 3 | 6 | 6 |
| A 1477-6 | 6 | 1 | 3 | 5 |
| A 1477-7 | 6 | 0 | 0 | 0 |
| A 1477-8 | 6 | 0 | 0 | 0 |
| A 1477-9 | 6 | 0 | 0 | 0 |
| A 1477-10 | 7 | 0 | 0 | 0 |
| A 1477-11 | 7 | 0 | 0 | 0 |
| A 1477-12 | 7 | 0 | 0 | 0 |
| A 1477-13 | 7 | 0 | 0 | 0 |
| A 1477-14 | 6 | 0 | 0 | 0 |
| A 1477-15 | 6 | 0 | 0 | 0 |
| A 1477-16 | 6 | 0 | 0 | 0 |

TABLE 10-continued

A. formidabilis BIOASSAY RESULTS

| Fraction | No of Larvae Injected | NUMBER SHOWING WRITHING AFTER | | |
|---|---|---|---|---|
| | | 24 hours | 48 hours | 72 hours |
| A 1477-17 | 6 | 0 | 0 | 0 |
| Saline Control | 6 | 0 | 0 | 0 |

TABLE 11

A. formidabilis TOXINS AMINO ACID ANALYSIS RESULTS

| | F1a exp | F1a pmol | F1a calc | F1b exp | F1b pmol | F1b calc |
|---|---|---|---|---|---|---|
| Asx | 4 | 614.7 | 3.93 | 6 | 430.7 | 6.39 |
| Glx | 1 | 172.1 | 1.10 | 4 | 282.5 | 4.19 |
| Ser | 3 | 448.4 | 2.87 | 4 | 276.6 | 4.10 |
| Gly | 4 | 625.2 | 3.99 | 2 | 156.5 | 2.32 |
| Arg | 2 | 294.6 | 1.88 | 2 | 128.25 | 1.91 |
| Thr | 3 | 466.8 | 2.99 | 4 | 266.5 | 3.96 |
| Ala | 3 | 470.6 | 3.00 | | | |
| Pro | 6 | 902.4 | 5.75 | 3 | 219.4 | 3.26 |
| Tyr | 1 | 166.7 | 1.02 | 1 | 70.32 | 1.05 |
| Val | 1 | 158.8 | 1.02 | 1 | 67.46 | 1.00 |
| Cys | 8 | N.D. | | 6 | N.D. | |
| Ile | 0 | | | 1 | 58.57 | 0.87 |
| Phe | 0 | | | 1 | 66.41 | 0.99 |
| Lys | 1 | 151.75 | 0.98 | 2 | 128.6 | 1.91 |

N.D. = not determined.

Industrial Application

The present invention provides toxins which can be used to provide insecticides for use in protecting commercially important crops.

REFERENCES

1. Quicke, D. (1988) Spiders Bite Their Way Towards Safer Insecticides. *New Scientist* (26.11.88),38–41.
2. Usherwood, P. N. R. (1985) The Action of Spider Toxins on the Insect Nerve Muscle System. In: *Approaches to New Leads for Insecticides* (Ed. von Keyserlingk, Jager and von Szczepanski; Springer Verlag, Berlin) pp.71–79.
3. Ross, D. C., Herzog, G. A., & Crimm, J. W. (1986) Peptide Toxins From Arthropod Venoms Disrupt Feeding and Utilization of Diet in the Cotton Bollworm. In: *Insect Neurochemistry and Neurophysiology* (Ed. Borkovec and Gelman; Humana Press, New Jersey) pp.401–404.
4. Branton, W. D., Kolton, L., Jan, Y. N., Jan, L. Y. (1987) Neurotoxins from Plectreurys Spider Venom are Potent Presynaptic Blockers in Drosophila. *J. Neuroscience* (December), 4195–4200.
5. Bowers, C. W., Phillips, H. S., Lee, P., Jan, Y. N., Jan, L. T. (1987) Identification and purification of an irreversible presynaptic neurotoxin from the venom of the spider *Hololena curta*. *Proc. Natl. Acad. Sci. USA* 84,3506–3510.
6. Skinner, W. S., Adams, M. E., Quistad, G. B., Katoaka, H., Cesarin, J., Enderlin, F. E. and Schooley, D. A. (1989) Purification and Characterisation of Two Classes of Neurotoxins from the Funnel Web Spider, *Agelenopsis aperta*. *J. Biol. Chem.* 264(4),2150–2155.
7. Adams, M. E., Bindokas, V. P., Hasegawa, L., Venema, V. J. (1990) ω-Agatoxins. Novel Calcium Channel antagonists of Two Subtypes from Funnel Web Spider (*Agelenopsis aperta*) Venom. *J. Biol. Chem.* 265(2), 861–867.

8. Sheumack, D. D., Claassens, R., Whiteley, N. M. and Howden, M. E. H. (1985) *FEBS Lett.* 181,154–156.
9. Brown, M. K., Sheumack, D. D., Tyler, M. I., Howden, M. E. H. (1988) Amino Acid Sequence of Versutoxin, a lethal neurotoxin from the venom of the Funnel-Web spider *Atrax versutus. Biochem. J.* 250,401–405.
10. Lipman D. J. and Pearson W. R. (1985) Rapid and sensitive protein similarity searches. Science 227,1435.
11. Teakle, R. E., and Jensen, J. M. (1985) *Heliothis punctigera.* In: *Handbook of Insect Rearing* Vol.2 (Ed. Singh and Moore); Elsevier Science, Amsterdam) pp.313–322.
12. Houmard J., Drapeau, G. R., (1972) Staphylococcal Protease: A proteolytic enzyme specific for glutamoyl bonds. *Proc. Natl. Acad. Sci. USA* 69, 3506–3509.
13. O'Shea, M. (1985) Neuropeptides in Insects: Possible Leads to New Control Methods. In: *Approaches to New Leads for Insecticides* (Ed. von Keyserlink, Jager and von Szczepanski; Springer Verlag, Berlin) pp.133–151.
14. Finney, D. J. (1971) Probit Analysis. 3rd Ed. Cambridge University Press, pp20–31.
15. Sheumack D. D., Baldo B. A., Carroll P. R., Hampson F., Howden M. E. H. and Skorulis A.(1984) A comparative study of properties and toxic constituents of funnel-web spider (Atrax) venoms. *Comp. Biochem. Physiol.* 78C (1),55–68.
16. Sutherland S. K. (1980) Antivenom to the venom of the male Sydney funnel-web spider *Atrax robustus. Med. J. Aust.* 2,437–441.
17. Higgins D. G., Bleasby A. J., Fuchs R. (1992) CLUSTAL V: improved software for multiple sequence alignment. *Computer Applications in the Biosciences (CABIOS),*8 (2): 189–191.
18. Stapleton A., Blankenship D. T., Ackemann B. L., Chen T. M., Gorder G. W., Manley G. D., Palfreyman M. G., Coutant J. E., Cardin A. D. (1990), Curatoxins: Neurotoxic Insecticidal polypeptides isolated from the funnel-web spider *Hololena curta J. Biol. Chem.* 265(4) 2054.
19. Loret E. P., Mansuelle P., Rochat H., Granier C. (1990) Neurotoxins Active on insects: Amino acid sequences, Chemical Modifications and secondary structure estimation by circular Dichroism of Toxins from the scorpion *Androctonus australis* Hector *Biochemistry* 29 1992.
20. Australian Patent Application No. 46881/89
21. Kopeyan C., Mansuelle P., Sampieri F., Brando T., Bahraoui E. M., Rochat H., Granier C. (1990) Primary structure of scorpion anti-insect toxins isolated from the venom of *Leiurus quinquestriatus quinquestriatus. FEBS LETT.* 261(2) 423.
22. Zilberberg N., Zlatkin E., Gurevitz M. (1991), The cDNA Sequence of a Depressant Insect Selective Neurotoxin from the Scorpion *Buthotus judaicus Toxicon* 29(9) 1155.

We claim:

1. An isolated polypeptide derived from spiders of the genus Atrax having a relative molecular mass of approximately 4000 a.m.u., said polypeptide comprising a sequence of about 36–37 amino acid residues, wherein residues in said sequence form 3 intrachain disulphide bridges, and said polypeptide is toxic to larval and adult insects.

2. The polypeptide according to claim 1 selected from the group consisting of In1, In2, In3, MR1, V1, F1a and F1b.

3. The polypeptide according to claim 1 which is produced recombinantly in a procaryotic microorganism or eukaryote.

4. The polypeptide according to claim 1 wherein said polypeptide is in carboxyamidated form.

5. An isolated polypeptide derived from spiders of the genus Hadronyche having a relative molecular mass of approximately 4000 a.m.u., said polypeptide comprising a sequence of about 36–37 amino acid residues, wherein residues in said sequence form 3 intrachain disulphide bridges, and said polypeptide is toxic to larval and adult insects.

6. The polypeptide according to claim 5 selected from the group consisting of In1, In2, In3, MR1, V1, F1a and F1b.

7. The polypeptide according to claim 5 which is produced recombinantly in a prokaryotic microorganism or a eukaryote.

8. The polypeptide according to claim 5 wherein said polypeptide is in carboxyamidated form.

* * * * *